United States Patent [19]

Link et al.

[11] Patent Number: 4,831,151

[45] Date of Patent: May 16, 1989

[54] ANTIMICROBIAL IMIDAZOLIUM DERIVATIVES

[75] Inventors: Helmut Link; Marc Montavon, both of Basel, Switzerland; Eva M. Karpitschka; Wilhelm Klötzer, both of Innsbruck, Austria; Renate Müssner, Innsbruck, Austria

[73] Assignee: Hoffmann-La Roche Inc., Nutley, N.J.

[21] Appl. No.: 853,831

[22] Filed: Apr. 21, 1986

[30] Foreign Application Priority Data

Apr. 26, 1985 [CH] Switzerland ............... 1778/85
Feb. 4, 1986 [CH] Switzerland ............... 410/86

[51] Int. Cl.$^4$ ............... A61K 31/415; C07D 233/60; C07D 233/56
[52] U.S. Cl. ............... 514/398; 514/211; 514/212; 514/218; 514/227.8; 514/228.2; 514/232.2; 514/232.5; 514/252; 514/253; 514/316; 514/318; 514/322; 514/326; 514/395; 514/397; 540/544; 540/553; 540/575; 540/603; 544/58.5; 544/60; 544/62; 544/82; 544/139; 544/357; 544/364; 544/370; 546/187; 546/193; 546/194; 546/199; 546/210; 548/327; 548/329; 548/336; 548/337
[58] Field of Search ............... 548/336, 337; 514/398, 514/397; 540/544, 553, 575, 603; 544/58.5, 60, 62, 82, 139, 357, 364, 370; 546/187, 193, 194, 199, 210

[56] References Cited

PUBLICATIONS

Karpitschka, Eva Maria; Elektrophile N–Aminierung von Dimethylxanthinen und Einfachen Imidazolen. Funktionelle Derivate der N–Aminoverbindungen. Innsbruck 1981, Universitat, Dissertation.
Mussner, Renate; Ueber N–Aminoderivate von 2-Methylimidazolene. Innsbruck 1982, Universitat, Kiplomarbeit.
Synthesis 1982, 592–594.
Chem. Pharm. Bull. 22, 482–484 (1974).
Chemical Abstracts 101, 2110040e (1984).

*Primary Examiner*—Richard A. Schwartz
*Attorney, Agent, or Firm*—Jon S. Saxe; George M. Gould; Julie M. Prlina

[57] ABSTRACT

Compounds of the formula

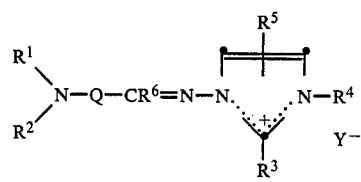

wherein the various substituents are defined hereinbelow and the pharmaceutically acceptable acid addition salts thereof, possess pharmacological properties. In particular, they possess antibacterial, antimycotic, protozoacidal and/or anthelmintic properties.

42 Claims, No Drawings

ANTIMICROBIAL IMIDAZOLIUM DERIVATIVES

SUMMARY OF THE INVENTION

The present invention is directed to imidazolium compounds of the general formula

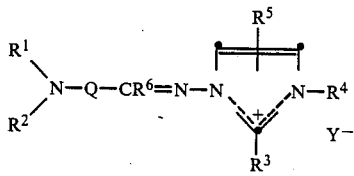

wherein the symbol Q signifies arylene or heteroarylene; the group $-NR^1R^2$ signifies a basic amino group; $R^3$ signifies hydrogen, lower alkyl, lower hydroxyalkyl, lower alkoxyalkyl or lower haloalkyl; $R^4$ signifies a basic amino group or the group $-N=CRc-Ra$, $-(NH)_n-CH(Rc)-Ra'$, $-NH-CO-Rb$ or $-CH_2-CO-Rb$; $R^5$ signifies hydrogen, lower alkyl, lower hydroxyalkyl, lower alkoxyalkyl, lower haloalkyl, aryl or a fused benzene ring; $R^6$ signifies hydrogen or lower alkyl; Ra signifies aryl, heteroaryl or a basic amino group; Ra' signifies aryl or heteroaryl; Rb signifies hydrogen, $-Q'$, $-OQ'$ or an aryl, heteroaryl or basic amino group which is optionally attached via a lower alkyl group; Rc signifies hydrogen or lower alkyl; n signifies the number 0 or 1; the dotted line signifies an additional double bond; the symbol Q' signifies a saturated or partially unsaturated lower hydrocarbon group which optionally contains one or two oxygen atoms in ethereal and/or alcoholic form; and the symbol $Y-$ signifies a pharmaceutically acceptable anion, and the pharmaceutically acceptable acid addition salts thereof.

Particular objects of the present invention are: the above compounds of formula I (insofar as $R^3$ has a significance other than hydrogen or methyl when $R^4$ signifies the group $-N=CH-Q-NR^1R^2$, $R^1$ and $R^2$ each signify methyl, $R^5$ and $R^6$ each signify hydrogen, Q signifies 1,4-phenylene and Y signifies chlorine) and the pharmaceutically acceptable acid addition salts thereof per se; a process and intermediates for their manufacture; the use of the intermediates for the manufacture of therapeutically active substances; the above compounds of formula I and the pharmaceutically acceptable acid addition salts thereof for use as therapeutically active substances; medicaments based on compounds of formula I and their pharmaceutically acceptable acid addition salts and their manufacture; the use of these compounds in the control or prevention of illnesses; as well as the use of these compounds for the manufacture of medicaments having antibacterial, antimycotic, protozoacidal and/or anthelmintic activity.

The term "lower" denotes residues and compounds with a maximum of 7, preferably a maximum of 4, carbon atoms. The term "alkyl" taken alone or in combinations such as "alkyl group", "alkoxy" and "alkylthio" denotes straight-chain or branched, saturated hydrocarbon residues such as methyl, ethyl, n-propyl, i-propyl, n-butyl, s-butyl, i-butyl and t-butyl. The term "saturated or partially unsaturated hydrocarbon group" denotes open-chain and cyclic groups and combinations thereof. Examples of saturated and partially unsaturated lower hydrocarbon groups are: lower alkyl groups such as methyl, ethyl, propyl, i-propyl, s-butyl and i-butyl; lower alkenyl groups such as 2-propenyl, 2-butenyl, 3-butenyl and 2-methyl-2-propenyl; lower cycloalkyl groups optionally substituted by lower alkyl groups such as cyclopropyl, cyclopentyl, 2-methylcyclopentyl, cyclohexyl and 3-methylcyclohexyl; cycloalkenyl groups optionally substituted by lower alkyl groups such as 3-cyclopentenyl, 1-methyl-3-cyclopentenyl and 3-cyclohexenyl; lower alkyl or alkenyl groups substituted by lower cycloalkyl or cycloalkenyl such as cyclopropylmethyl, cyclopropylethyl, cyclopentylmethyl, cyclohexylmethyl, 2-cyclohexenylmethyl and 3-cyclopropyl-2-propenyl. Examples of saturated or partially unsaturated lower hydrocarbon groups which contain one or two oxygen atoms in ethereal and/or alcoholic form are: lower alkoxyalkyl groups such as methoxymethyl, ethoxymethyl and 2,2-diethoxyethyl, and lower hydroxyalkyl groups such as hydroxymethyl, 1-hydroxyethyl and 2-hydroxyethyl.

The term "aryl" denotes carbocyclic aromatic groups, preferably mono- or bicyclic groups, especially phenyl and naphthyl groups, which are optionally substituted by a basic amino group and which, in addition, can be substituted by one or two substituents from the group consisting of lower alkyl, lower alkoxy, lower alkylthio, lower alkanoyl, lower alkoxycarbonyl, aryl, halogen, trifluoromethyl, hydroxy, nitro and cyano. The term "arylene" denotes carbocyclic aromatic groups with two free valencies, preferably mono- or

DETAILED DESCRIPTION OF THE INVENTION

The present invention is directed to imidazolium compounds of the general formula

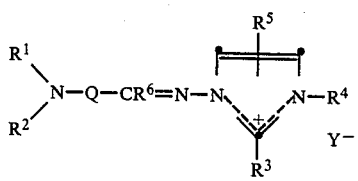

wherein the symbol Q signifies arylene or heteroarylene; the group $-NR^1R^2$ signifies a basic amino group; $R^3$ signifies hydrogen, lower alkyl, lower hydroxyalkyl, lower alkoxyalkyl or lower haloalkyl; $R^4$ signifies a basic amino group or the group $-N=CRc-Ra$, $-(NH)_n-CH(Rc)-Ra'$, $-NH-CO-Rb$ or $-CH_2-CO-Rb$; $R^5$ signifies hydrogen, lower alkyl, lower hydroxyalkyl, lower alkoxyalkyl, lower haloalkyl, aryl or a fused benzene ring; $R^6$ signifies hydrogen or lower alkyl; Ra signifies aryl, heteroaryl or a basic amino group; Ra' signifies aryl or heteroaryl; Rb signifies hydrogen, $-Q'$, $-OQ'$ or an aryl, heteroaryl or basic amino group which is optionally attached via a lower bicyclic groups, especially 1,4- or 1,2-phenylene and 1,4- or 1,2-naphthylene groups, which can be substituted by one or two substituents from the group consisting of lower alkyl, lower alkoxy, lower alkylthio, lower alkanoyl, lower alkoxycarbonyl, aryl, halogen, trifluoromethyl, hydroxy, nitro and cyano.

The term "heteroaryl" denotes heterocyclic aromatic groups, preferably mono- or bicyclic groups, especially 5- or 6-membered aromatic heterocycles (optionally fused with a benzene ring), which are optionally substituted by a basic amino group and which, in addition, can be substituted by one or two substituents from the group consisting of lower alkyl, lower alkoxy, lower alkylthio, lower alkanoyl, lower alkoxycarbonyl, aryl, halogen, trifluoromethyl, hydroxy, nitro and cyano. The 5-membered aromatic heterocycles preferably contain as the hetero ring member(s) an oxygen or sulphur atom or an imino grouping and optionally a further one or two nitrogen atoms. The 6-membered aromatic heterocycles preferably contain as the ring member(s) one, two or three nitrogen atoms. The term "heteroarylene" denotes heterocyclic aromatic groups with two free valencies, preferably mono- or bicyclic groups, especially 5- and 6-membered aromatic heterocycles (optionally fused with a benzene ring) with two free valencies, which can be substituted by one or two substituents from the group consisting of lower alkyl, lower alkoxy, lower alkylthio, lower alkanoyl, lower alkoxycarbonyl, aryl, halogen, trifluoromethyl, hydroxy, nitro and cyano.

The term "halogen" denotes the four forms fluorine, chlorine, bromine and iodine.

The term "basic amino group" denotes unsubstituted or mono- or disubstituted amino groups with basic character. The basic amino groups can be represented by the general formula $-NR^1R^2$. In this formula $R^1$ preferably signifies hydrogen or lower alkyl and $R^2$ preferably signifies hydrogen or a saturated or partially unsaturated lower hydrocarbon group which optionally contains one or two oxygen atoms in ethereal and/or alcoholic form or $R^1$ and $R^2$ together with the nitrogen atom preferably signify a 5- to 7-membered saturated N-heterocycle which is optionally substituted by one or two lower alkyl groups and which can contain as a ring member in place of one methylene group an oxygen or sulphur atom or the group >SO, >SO$_2$, >CO, >CH—Rd or >N—Re in which Rd signifies hydroxy, lower alkanoyl, lower alkoxycarbonyl, carbamoyl, mono- or di(lower alkyl)carbamoyl or a saturated or partially unsaturated lower hydrocarbon group which is optionally attached via an oxygen atom and which optionally contains, in addition, one or two oxygen atoms in ethereal and/or alcoholic form and Re signifies hydrogen, lower alkanoyl, lower alkoxycarbonyl, carbamoyl, mono- or di(lower alkyl)carbamoyl or a saturated or partially unsaturated lower hydrocarbon group which optionally contains one or two oxygen atoms in ethereal and/or alcoholic form.

If a compound of formula I contains more than one basic amino group, then these groups can be the same or different.

A preferred embodiment of the present invention is directed to compounds of formula I above in which $R^4$ signifies the group $-N=CR^6-Q-NR^1R^2$, i.e. compounds of the general formula

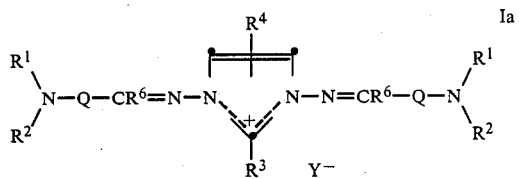

wherein $R^1$, $R^2$, $R^3$, $R^5$, $R^6$, Q and $Y^-$ have the above significance, and whereby the symbols Q, $R^1$, $R^2$ and $R^6$ in each case can be the same or different.

The symbol Q preferably signifies 1,4-phenylene or 1,4-naphthylene which is optionally substituted by one or two substituents from the group consisting of lower alkyl and lower alkoxy. In an especially preferred embodiment the symbol Q signifies 1,4-phenylene.

$R^1$ and $R^2$ each preferably signify hydrogen or lower alkyl or together with the nitrogen atom signify 4-morpholinyl, 1-piperazinyl, 4-(lower alkyl)-1-piperazinyl, 4-(lower alkoxycarbonyl)-1-piperazinyl or 1-pyrrolidinyl which is optionally substituted by one or two lower alkyl groups. In an especially preferred embodiment $R^1$ and $R^2$ each signify lower alkyl.

$R^3$ preferably signifies lower alkyl, with lower alkyl groups having at least 2 carbon atoms being especially preferred.

Insofar as the symbol $R^4$ does not signify the group $-N=CR^6-Q-NR^1R^2$, it preferably signifies the group $-N=CRc-Ra$ or $-CH_2-CO-Rb$ in which Ra preferably signifies phenyl which is optionally substituted by one or two substituents from the group consisting of lower alkyl, lower alkoxy, lower alkylthio, lower alkanoyl, lower alkoxycarbonyl, halogen, trifluoromethyl, hydroxy, nitro and cyano and Rb preferably signifies lower alkyl, lower alkoxy or phenyl which is optionally substituted by one or two substituents from the group consisting of lower alkyl, lower alkoxy, lower alkylthio, lower alkanoyl, lower alkoxycarbonyl, halogen, trifluoromethyl, hydroxy, nitro and cyano.

The symbols $R^5$, $R^6$ and Rc preferably signify hydrogen.

The imidazolium salts listed hereinafter are representatives of the class of substance defined by general formula I:

1,3-Bis[[p-(dimethylamino)benzylidene]amino]imidazolium salts,
3-[p-chlorobenzylidene)amino]-1-[[p-(dimethylamino)benzylidene]amino]-2-ethylimidazolium salts,
3-[p-(dimethylamino)phenacyl]-1-[[p-(dimethylamino)benzylidene]amino]-2-ethylimidazolium salts,
1,3-bis[[p-(dimethylamino)benzylidene]amino]-2-methylimidazolium salts,
1,3-bis[[p-(dimethylamino)benzylidene]amino]-2-ethylimidazolium salts,
1-[[p-(dimethylamino)benzylidene]amino]-2-ethyl-3-[(p-nitrobenzylidene)amino]imidazolium salts and
1,3-bis[[p-(dimethylamino)benzylidene]amino]-2-propyl-imidazolium salts.

The novel compounds of formula I and their pharmaceutically acceptable acid additions salts can be manufactured in accordance with the invention by (a) reacting a compound of the general formula

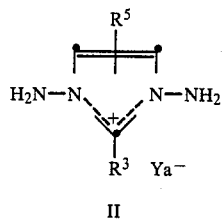 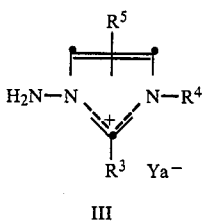

II         III

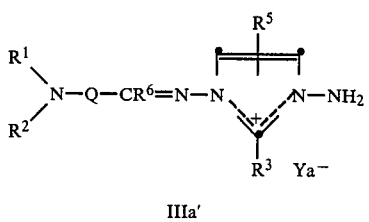

IIIa' wherein $R^1$, $R^2$, $R^3$, $R^4$, $R^5$, $R^6$ and Q have the above significance and $Ya^-$ signifies an anion, with a carbonyl compound of the general formula

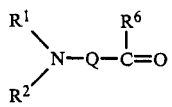

IVa or, respectively, Ra'—C(Rc)=O IVb or Ra*—CRc(OR')$_2$ IVc
wherein $R^1$, $R^2$, $R^6$, Ra', Rc and Q have the above significance, Ra* signifies a basic amino group and R' signifies lower alkyl, or (b) reacting a compound of the general formula

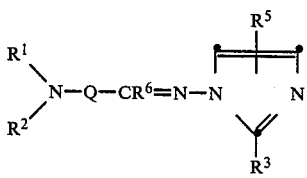

Va' wherein $R^1$, $R^2$, $R^3$, $R^5$, $R^6$ and Q have the above significance, with a compound of the general formula

         VI wherein $R^{41}$ signifies the group —CH(Rc)—Ra' or —CH$_2$—CO—Rb, X signifies a leaving group and Ra', Rb and Rc have the above significance, or (c) reacting a compound of formula IIIa' above with a compound of the general formula

         VIa wherein Ra', Rc and X have the above significance, or (d) reacting a compound of formula IIIa' above with a compound of the general formula

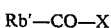         XIII wherein Rb' signifies hydrogen, —Q', —OQ', aryl, heteroaryl, a secondary basic amino group or an aryl, heteroaryl or basic amino group which is attached via a lower alkyl group and Q' and X have the above significance, or (e) reacting a compound of the general formula

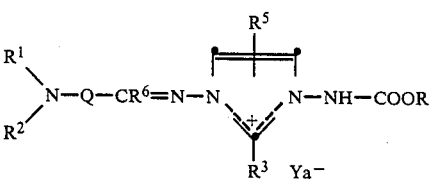

VII wherein $R^1$, $R^2$, $R^3$, $R^5$, $R^6$, Q and $Ya^-$ have the above significance and R signifies phenyl which is optionally substituted by lower alkyl, lower alkoxy or halogen, with ammonia or a corresponding basic primary or secondary amine, (f) optionally replacing the anion denoted by $Ya^-$ in a compound obtained by a pharmaceutically acceptable anion and (g) if desired, converting of formula I obtained into a pharmaceutically acceptable salt.

In several of the above processes in accordance with the invention it is necessary to block by protecting groups any reactive amino and/or hydroxyl groups present in the starting materials. These cases are readily recognisable by the person skilled in the art and the choice of the respective suitable protecting groups also presents no problems to him.

The reaction of amines with aldehydes, ketones or acetals in accordance with process variant (a) is a reaction which is known per se and which is familiar to any person skilled in the art. As solvents there are suitable, for example, lower fatty acids such as acetic acid and propionic acid, lower alcohols such as methanol, ethanol and 2-propanol, lower fatty acid esters such as ethyl acetate, lower ethers such as diethyl ether, t-butyl methyl ether, ethylene glycol dimethyl ether, tetrahydrofuran and dioxan, halogenated lower hydrocarbons such as methylene chloride, chloroform and ethylene chloride, aromatic hydrocarbons such as benzene, toluene and xylene, acetonitrile, N,N-dimethylformamide and dimethyl sulphoxide. The reaction temperature is not critical. The reaction can be carried out, for example, in a range of about 0° C. up to the boiling temperature of the chosen solvent. However, the reaction is preferably carried out at room temperature. In the reaction with the less reactive ketones and ketals of formula IV (Rc=lower alkyl) there is preferably used a condensation agent such as triethyloxonium tetrafluoroborate.

Compounds of formula I in which $R^4$ signifies the group —CH(Rc)—Ra' or —CH$_2$—CO—Rb can be manufactured in accordance with process variant (b) by alkylating imidazole derivatives of formula Va'. This is also a reaction which is known per se and which is familiar to any person skilled in the art. Suitable solvents are, for example, halogenated lower hydrocarbons such as methylene chloride, chloroform and ethylene chloride, open-chain or cyclic ethers such as diethyl ether, t-butyl methyl ether, ethylene glycol dimethyl ether, tetrahydrofuran and dioxan, lower fatty acid esters such as ethyl acetate, lower alcohols such as methanol, ethanol and i-propanol, aromatic hydrocarbons such as benzene, toluene and xylene, acetonitrile, N,N-dimethylformamide and dimethyl sulphoxide. The reaction temperature is not critical. For example, the reaction can be carried out in a range of about 0° C. up to the boiling temperature of the solvent.

Compounds of formula I in which $R^4$ signifies the group —NH—CH(Rc)—Ra' can be manufactured in accordance with process variant (c) by alkylating amines of formula IIIa'. This is also a reaction which is known per se and which is familiar to any person skilled in the art. As solvents there are suitable especially polar solvents, for example lower alcohols such as methanol, ethanol, i-propanol, open-chain and cyclic ethers such as ethylene glycol dimethyl ether, tetrahydrofuran and dioxan, N,N-dimethylformamide and dimethyl sulphoxide. The reaction temperature is not critical and the reaction can be carried out, for example, in a range of about 0° C. up to the boiling temperature of the chosen solvent.

Compounds of formula I in which $R^4$ signifies the group —NH—CO—Rb' and Rb' signifies hydrogen, aryl, heteroaryl, a secondary basic amino group, an aryl, heteroaryl or basic amino group which is attached via a lower alkyl group or a saturated or partially unsaturated lower hydrocarbon group which is optionally attached via an oxygen atom and which optionally contains one or two oxygen atoms in ethereal and/or alcoholic form can be manufactured in accordance with process variant (d) by acylating amines of formula IIIa'. This is also a reaction which is known per se and which is familiar to any person skilled in the art. Suitable solvents are especially the polar solvents mentioned above. The reaction temperature is not critical. The reaction can be carried out in a range of about 0° C. up to the boiling temperature of the chosen solvent. However, the reaction is preferably carried out in a range of about 0° C. to room temperature.

Compounds of formula I in which $R^4$ signifies the group —NH—CO—Rb″ and Rb″ signifies a basic amino group can be manufactured with process variant (e) by amidating compounds of formula VII. This is also a reaction which is known per se and which is familiar to any person skilled in the art. Suitable solvents are, for example, open-chain and cyclic ethers such diethyl ether, t-butyl methyl ether, tetrahydrofuran and dioxan, N,N-dimethylformamide and dimethyl sulphoxide. The reaction temperature is not critical and the reaction can be carried out, for example, in a range of about 0° C. up to the boiling temperature of the chosen solvent. However, the reaction is preferably carried out at room temperature.

The anion denoted by $Ya^-$ in a compound obtained can be replaced by a pharmaceutically acceptable anion in accordance with process variant (f). This replacement reaction is also a reaction which is known per se and which is familiar to any person skilled in the art. There are preferably used conventional ion exchangers which are loaded with a pharmaceutically acceptable anion.

Compounds of formula I can be converted in to pharmaceutically acceptable acid addition salts in accordance with process variant (g). Such acid addition salts can be manufactured according to methods which are known per se and which are familiar to any person skilled in the art. In this case there come in to consideration not only salts with inorganic acids, but also salts with organic acids, for example hydrochlorides, hydrobromides, sulphates, nitrates, citrates, acetates, maleates, succinates, methanesulphonates, p-toluenesulphonates and the like.

The various compounds which are mentioned as starting materials can be prepared in accordance with the following Reaction Scheme I in which $R^1$, $R^2$, $R^3$, $R^{41}$, $R^5$, $R^6$, Ra, Ra', Rb', Rb″, Rc, R, Q and $Ya^-$ have the above significance.

Reaction Scheme I

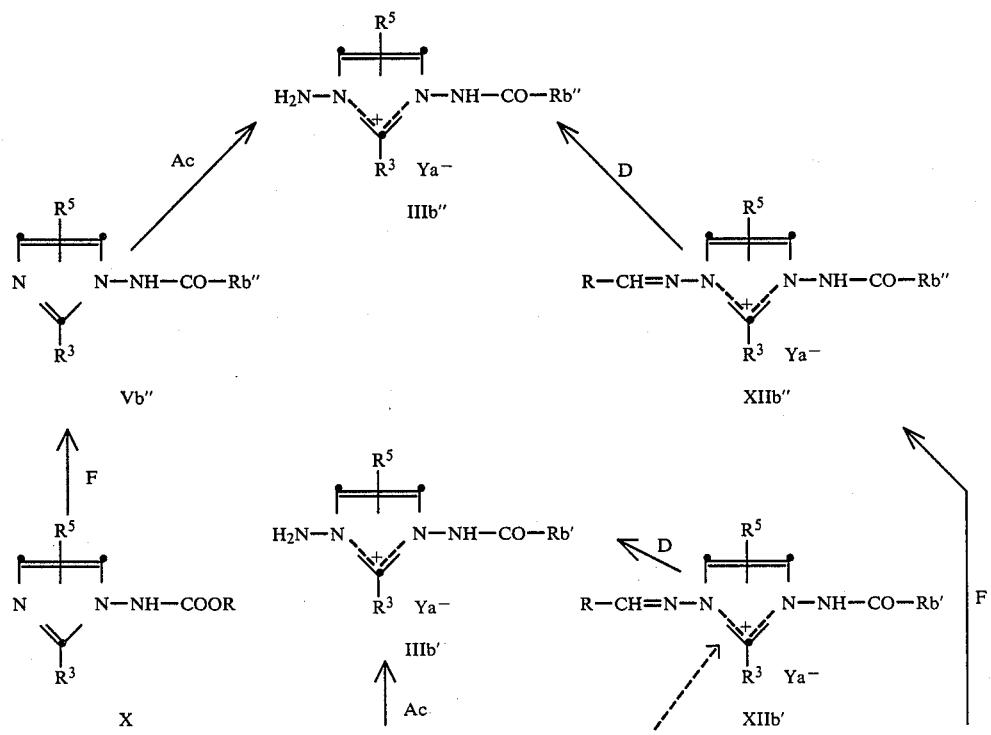

-continued
Reaction Scheme I

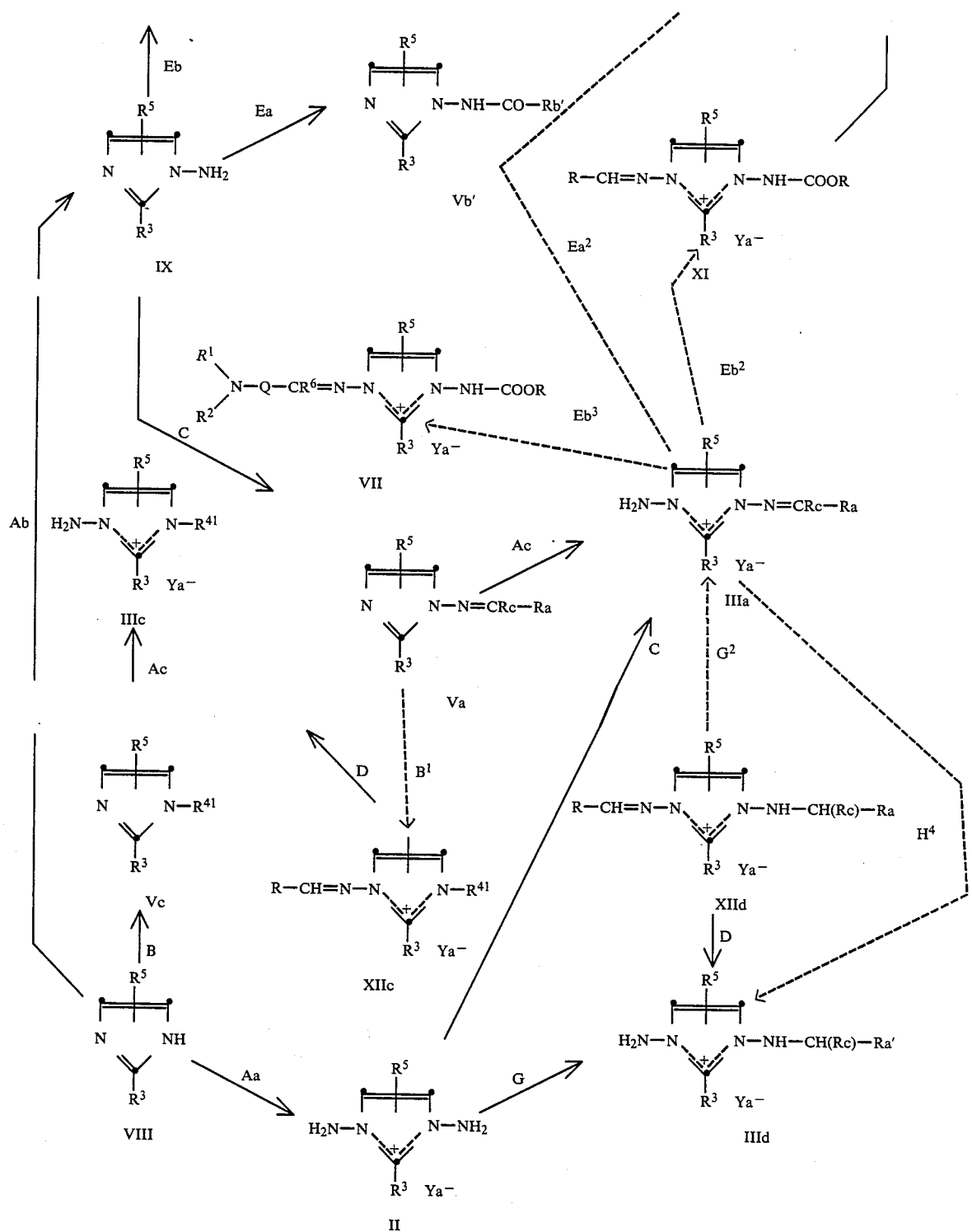

The dotted arrows signify that not all of the given starting materials come into consideration for the reaction in question; see the following details for the reference numerals (1) to (4).

(1) Starting materials for this reaction are compounds of formula Va in which Ra signifies phenyl which is optionally substituted by lower alkyl, lower alkoxy or halogen and Rc signifies hydrogen.

(2) Starting materials for this reaction are compounds of formula IIIa in which Ra signifies phenyl which is optionally substituted by lower alkyl, lower alkoxy or halogen and Rc signifies hydrogen.

(3) Starting materials for this reaction are compounds of formula IIIa in which the group =CRc—Ra signifies the group =C(R$^6$)—Q—NR$^1$R$^2$ and Q, R$^1$, and R$^2$ and R$^6$ have the above significance.

(4) Starting materials for this reaction are compounds of formula IIIa in which Ra signifies aryl or heteroaryl.

In the case of reaction steps A to H which are illustrated in more detail hereinafter the reactions are without exception known per se and familiar to any person skilled in the art.

Aa: This reaction step is an electrophilic amination with an electrophilic aminating agent such as hydroxylamine O-sulphonic acid or its salts with inorganic bases. Preferably, the corresponding alkali metal salts, for example the sodium salt, are used and the reaction is carried out in aqueous solution. In this case there is obtained as a rule a mixture consisting of the diamine of formula II and the monoamine of formula IX. The two compounds can be separated from each other according to methods which are known per se and which are familiar to any person skilled in the art. The Examples below contain detailed information concerning the separation of the mixtures obtained.

Ab: This reaction step is an electrophilic amination with an electrophilic aminating agent such as O-diphenylphosphinylhydroxylamine, whereby the compound of formula VIII is converted with a strong base into an alkali metal salt prior to the reaction with the electrophilic aminating agent. Suitable bases are, for example, lower alkali metal alkoxides such as sodium methoxide and sodium ethoxide and alkali metal hydrides such as sodium hydride. Suitable solvents are, for example, N-methylpyrrolidone, N,N-dimethylformamide, lower alcohols, ethers such as tetrahydrofuran, diethylene glycol dimethyl ether, diethylene glycol diethyl ether and diethylene glycol dibutyl ether. The reaction temperature preferably lies in a range of about 0° C. to 100° C., with the reaction being preferably carried out at room temperature.

Ac: This reaction step is an electrophilic animation with an electrophilic aminating agent such as O-diphenylphosphinylhydroxylamine. Suitable solvents are, for example, halogenated lower hydrocarbons such as chloroform, methylene chloride and ethylene chloride, ethers such as diethyl ether and tetrahydrofuran, lower alcohols such as ethanol, acetonitrile, N,N-dimethylformamide, dimethyl sulphoxide and mixtures thereof. The reaction temperature lies in a range of about 0° C. up to the boiling temperature of the chosen solvent. The reaction is preferably carried out at room temperature.

B: In this reaction step the corresponding starting material is reacted with a compound of formula VI above. Suitable solvents are, for example, halogenated lower hydrocarbons such as methylene chloride, chloroform and ethylene chloride, open-chain and cyclic ethers such as diethyl ether, diisopropyl ether, ethylene glycol dimethyl ether, diethylene glycol diethyl ether, tetrahydrofuran and dioxan, acetonitrile and N,N-dimethylformamide. This reaction can be carried out in a temperature range of about 0° C. to the boiling temperature of the chosen solvent.

C: In this reaction step the corresponding starting material is reacted with an aldehyde or ketone of formula IV above to give the corresponding aldimine or ketimine, respectively. Suitable solvents are, for example, lower fatty acids such as acetic acid and propionic acid, lower alcohols such as methanol, ethanol and 2-propanol, halogenated lower hydrocarbons such as methylene chloride, chloroform and ethylene chloride, open-chain and cyclic ethers such as diethyl ether, diisopropyl ether, t-butyl methyl ether, ethylene glycol dimethyl ether, diethylene glycol diethyl ether, tetrahydrofuran and dioxan, acetonitrile, N,N-dimethylformamide and dimethyl sulphoxide. The reaction can be carried out in a temperature range of about 0° C. to the boiling temperature of the chosen solvent. The reaction is preferably carried out at room temperature. In the reaction with the less active ketones and ketals of formula IV (Rc=lower alkyl) there is preferably used a condensation agent such as triethyloxonium tetrafluoroborate.

D: This reaction step comprises the hydrolysis of an aldimine. In a preferred embodiment the corresponding starting material is treated with an aqueous acid and the aromatic aldehyde obtained is removed by steam distillation. Suitable acids are, for example, diluted hydrochloric acid and diluted hydrobromic acid.

Ea: In this reaction step the corresponding starting material is reacted with a compound of formula XIII above. Suitable solvents are, for example, halogenated lower hydrocarbons such as methylene chloride, chloroform and ethylene chloride, open-chain and cyclic ethers such as diethyl ether, diisopropyl ether, t-butyl methyl ether, tetrahydrofuran and dioxan, lower fatty acid esters such as ethyl acetate and methyl acetate, and acetonitrile. The reaction can be carried out in a temperature range of about 0° C. to the boiling temperature of the chosen solvent.

Eb: This reaction is an acylation with a compound of the general formula

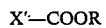

$$X'\text{—COOR} \qquad \qquad XIV$$

wherein X' signifies halogen and R has the above significance.

This reaction can be carried out under the same conditions as the reaction step denoted by Ea.

F: In this reaction step the corresponding starting material is reacted with ammonia or a corresponding basic primary or secondary amine. Suitable solvents are, for example, open-chain and cyclic ethers such as diethyl ether, tetrahydrofuran and dioxan, N,N-dimethylformamide and dimethyl sulphoxide. The reaction can be carried out in a range of about 0° C. up to the boiling temperature of the chosen solvent. However, the reaction is conveniently carried out at room temperature.

G: In this reaction step the corresponding starting material is reacted with a comnpound of formula VIa above. Suitable solvents are, for example, open-chain and cyclic ethers such as diethyl ether, tetrahydrofuran and dioxan, N,N-dimethylformamide and dimethyl sulphoxide. The reaction can be carried out in a range of about 0° C. up to the boiling temperature of the chosen solvent. However, the reaction is conveniently carried out at room temperature.

H: In this reaction step the aldimine or ketimine used as the starting material is reduced to the corresponding amine. The reduction is preferably carried out with elementary hydrogen in the presence of a suitable catalyst. Suitable catalysts are, for example, palladium/carbon and platinum oxide. Suitable solvents are especially lower alcohols such as methanol and ethanol. The reduction is preferably carried out at room temperature.

The above-described novel compounds which are used as starting materials and their use for the manufacture of therapeutically active substances which have as a common structural feature a group of the general formula

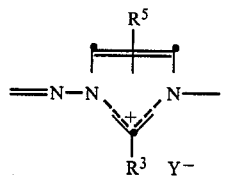

wherein $R^3$, $R^5$ and $Y^-$ have the above significance, are also an object of the present invention. These are the above-defined compounds of formulae II, III (insofar as $R^3$ has a significance other then hydrogen or methyl) and VII and the compounds of the general formulae

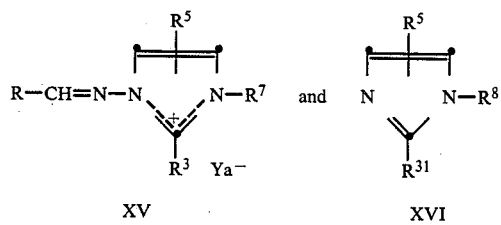

wherein $R^7$ signifies the group $-(NH)_n-CH(Rc)-Ra'$, $-NH-CO-Rb$, $-CH_2-CO-Rb$ or $-NH-COOR$, $R^8$ signifies the group $-N=CRc-Ra$, $-CH(Rc)-Ra'$, $-NH-CO-Rb$, $-CH_2-CO-Rb$ or $-NH-COOR$, $R^{31}$ signifies lower alkyl with at least two carbon atoms, lower hydroxyalkyl, lower alkoxyalkyl or lower haloalkyl and R, $R^3$, $R^5$, Ra, Ra', Rb, Rc, $Ya^-$ and n have the above significance.

As mentioned earlier, the compounds of formula I possess valuable pharmacological properties. For example, they exhibit antiparasitic properties and are especially active against parasitic protozoa and worms. Their activity against parasitic worms, especially against nematodes such as the filaria, is especially pronounced. These pharmacological properties can be determined by means of test methods which are known and which are familiar to any person skilled in the art.

The filaricidal activity of the compounds of formula I can be determined, for example, on cotton rats (Sigmodon hispidus) which have been infected with Litomosoides carinii. The infection with L. carinii is transmitted by the blood-sucking mite Bdellonyssus bacoti in which the development of the microfilaria to infectious larvae takes place. The cotton rats are infected by exposing them to bites of infected mites. 14 weeks after the infection groups of 2-4 animals are treated subcutaneously with the compound to be tested. 42 days after treatment with the compound to be tested the experimental animals are dissected, whereby the adult filaria are removed from the pleural cavity. Living and dead or encapsulated worms are separated from one another and weighed. The filaricidal activity is expressed as the percentage proportion of dead macrofilaria per treatment group. The $ED_{90}$ is then determined by means of Prohibit analysis using the values from different dosage groups. The $ED_{90}$ is that dosage at which 90% of the worms removed from the pleural cavity are dead. In the following Table there are compiled the results which have been obtained in the previously described test with representative members of the class of compound defined by general formula I. Moreover, the Table contains data concerning the acute toxicity of some of these compounds in mg per kg in the case of single oral administration to mice.

TABLE

Compounds of formula I in which $R^5$ and $R^6$ = hydrogen and in which:

| $R^1$ | $R^2$ | Q | $R^3$ | $R^4$ | $Y^-$ | $ED_{90}$ (mg/kg s.c.) | $LD_{50}$ (mg/kg p.o.) |
|---|---|---|---|---|---|---|---|
| $CH_3-$ | $CH_3-$ | 1,4-Phenylene | $CH_3-$ | $-N=CH-\langle\text{phenyl}\rangle-N(CH_3)_2$ | $Cl^-$ | 1.6 | 80-156 |
| $CH_3-$ | $CH_3-$ | 1,4-Phenylene | $CH_3-$ | $-N=CH-\langle\text{phenyl}\rangle-N(CH_3)_2$ | $CH_3COO^-$ | 0.85 | — |
| $CH_3-$ | $CH_3-$ | 1,4-Phenylene | $C_2H_5-$ | $-N=CH-\langle\text{phenyl}\rangle-N(CH_3)_2$ | $Cl^-$ | 0.4 | 62.5-125 |
| $CH_3-$ | $CH_3-$ | 1,4-Phenylene | $C_2H_5-$ | $-N=CH-\langle\text{phenyl}\rangle-N(CH_3)_2$ | $CH_3COO^-$ | 0.25 | — |
| $CH_3-$ | $CH_3-$ | 1,4-Phenylene | $CH_3(CH_2)_2-$ | $-N=CH-\langle\text{phenyl}\rangle-N(CH_3)_2$ | $Cl^-$ | <0.25 | 62.5-125 |

TABLE-continued

Compounds of formula I in which $R^5$ and $R^6$ = hydrogen and in which:

| $R^1$ | $R^2$ | Q | $R^3$ | $R^4$ | $Y^-$ | ED$_{90}$ (mg/kg s.c.) | LD$_{50}$ (mg/kg p.o.) |
|---|---|---|---|---|---|---|---|
| CH$_3$— | CH$_3$— | 1,4-Phenylene | CH$_3$(CH$_2$)$_3$— | —N=CH—⟨C$_6$H$_4$⟩—N(CH$_3$)$_2$ | Cl$^-$ | <0.25 | — |
| CH$_3$— | CH$_3$— | 1,4-Phenylene | C$_2$H$_5$— | —N=CH—⟨C$_6$H$_4$⟩—NO$_2$ | Cl$^-$ | <1 | — |
| C$_2$H$_5$— | C$_2$H$_5$— | 1,4-Phenylene | C$_2$H$_5$— | —N=CH—⟨C$_6$H$_4$⟩—N(C$_2$H$_5$)$_2$ | Cl$^-$ | 0.75 | — |
| CH$_3$— | CH$_3$— | 1,4-Naphthylene | C$_2$H$_5$— | —N=CH—⟨naphthyl⟩—N(CH$_3$)$_2$ | Cl$^-$ | 3 | 312–625 |

The compounds of formula I can be used as medicaments, e.g. in the form of pharmaceutical preparations for enteral or parental application. They can be administered, for example, perorally, e.g. in the form of tablets, coated tablets, dragees, hard and soft gelatine capsules, solutions, emulsions or suspensions, rectally, e.g. in the form of suppositories, or parenterally, e.g. in the form of injection solutions.

The manufacture of the pharmaceutical preparations can be carried out in a manner which is familiar to any person skilled in the art by bringing the described substances, optionally in combination with other therapeutically valuable substances, into a galenical administration form together with suitable, non-toxic, inert, therapeutically compatible solid or liquid carrier materials and, if desired, the usual pharmaceutical adjuvants.

As carrier materials there are suitable not only inorganic carrier materials, but also organic carrier materials. Thus, for tablets, coated tablets, dragees and hard gelatine capsules there can be used as carrier materials, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance no carriers are, however, required in the case of soft gelatine capsules). Suitable carrier materials for the manufacure of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example, natural or hardened oils, waxes, fats and semi-liquid or liquid polyols.

As pharmaceutical adjuvants there come into consideration the usual stabilizing, preserving, wetting and emulsifying agents, flavour-improving agents, salts for varying the osmotic pressure, buffer substances, solubilizers, coloring agents, coating agents and antioxidants.

The dosage of the described substances can vary within wide limits depending on the illness to be treated, the age and the individual condition of the patient and on the mode of administration and will, of course, be adjusted to the individual requirements in each particular case. For the prophylaxis and therapy of infectious diseases which are caused by bacteria, fungi or parasites there comes into consideration for adult patients a daily dosage of about 0.01 g to about 4 g, especially about 0.05 g to about 2 g. Depending on the dosage it is convenient to administer the daily dosage in several unit dosages.

The pharmaceutical preparations in accordance with the invention conveniently contain about 10–1000 mg, preferably 50–500 mg, of a substance in accordance with the invention.

The following Examples illustrate the present invention in more detail. However, they are not intended to limit its extent in any manner. All temperatures are given in degrees Celsius.

EXAMPLE 1

(a) A solution of 21.2 g (211 mmol) of 2-ethylimidazole in 70 ml of water is treated within 30 minutes with a solution, prepared at 0°, of 25.0 g (221 mmol) of hydroxylamine O-sulphonic acid and 18.5 g (220 mmol) of sodium hydrogen carbonate in 150 ml of water. In so doing the reaction solution warms to about 30°. The solution is stirred at room temperature for 20 hours, acidified with 65 ml of 2N hydrochloric acid, a solution of 15.5 g (146 mmol) of benzaldehyde in 50 ml of ether is added thereto and the mixture is stirred 6 hours. The precipitated product is filtered off and recrystallized from methanol. There is obtained 1,3-bis(-benzylideneamino)-2-ethyl-imidazoliumbenzaldoxime O-sulphonate of melting point 180°–182°.

The mother liquor is washed with ether, neutralized with 3N sodium hydroxide solution and extracted with methylene chloride. After drying the extract over sodium sulphate, evaporation and crystallization of the thus-obtained material from ether/petroleum ether there is obtained 1-benzylideneamino-2-ethylimidazole of melting point 67°–68°.

2.5 g (7.4 mmol) 1,3-bis(benzylideneamino)-2-ethyl-imidazolium-benzaldoxime O-sulphonate, 20 ml of water and 9.2 ml of 2N hydrochloric acid are warmed on a steam-bath, whereby the resulting benzaldehyde is removed by steam distillation. The solution obtained is evaporated in vacuo. The residue remaining behind is placed on a column loaded with 20 g of Amberlite IRA 400 (chloride), whereupon elution is carried out with water. The aqueous solution is evaporated (finally in a high vacuum) and the residue is crystallized from ethanol/ether. There is obtained 1,3-diamino-2-ethyl-imidazolium chloride as white crystals of melting point 181°–182°.

A solution of 19.9 g (0.1 mol) of 1-benzylideneamino-2-ethyl-imidazole in 200 ml of 1.5N hydrochloric acid is subjected to a steam distillation until benzaldehyde no longer results. The mixture is evaporated and the product obtained is recrystallized from ethanol/ether. There are obtained 14.5 g of 1-amino-2-ethylimidazole hydrochloride of melting point 90°–91°.

In an analogous manner:

(b) From 2-(hydroxymethyl)imidazole there is obtained 1,3-bis(benzylideneamino)-2-(hydroxymethyl)-imidazolium chloride of decomposition point 230° C. and 1-benzylideneamino-2-(hydroxymethyl)-imidazole of melting point 136°–138°;

from 1,3-bis(benzylideneamino)-1-(hydroxymethyl)-imidazolium chloride there is obtained 1,3-diamino-2-(hydroxymethyl)-imidazolium chloride of melting point 126°–128°;

from 1-benzylideneamino-2-(hydroxymethyl)-imidazole there is obtained 1-amino-2-(hydroxymethyl)imidazole hydrochloride of melting point 150°–152°;

(c) from 4-methylimidazole there is obtained 1,3-bis(-benzylideneamino)-4-methylimidazolium chloride of decomposition point 137°–139°;

from 1,3-bis(benzylideneamino)-4-methylimidazolium chloride there is obtained 1,3-diamino-4-methylimidazolium chloride of melting point 194°–196° (recrystallized from ethanol);

(d) from 4-(hydroxymethyl)imidazole there is obtained 1,3-bis(benzylideneamino)-4-(hydroxymethyl-)imidazolium chloride of melting point 173°–175°;

from 1,3-bis(benzylideneamino)-3-(hydroxymethyl)-imidazolium chloride there is obtained 1,3-diamino-4-(hydroxymethyl)imidazolium chloride of melting point 60°–61°;

(e) from 2-(ethoxymethyl)imidazole there is obtained 1,3-bis(benzylideneamino)-2-(ethoxymethyl-)imidazolium chloride of melting point 205°–206° (recrystallized from ethanol);

from 1,3-bis(benzylideneamino)-2-(ethoxymethyl)-imidazolium chloride there is obtained 1,3-diamino-2-(ethoxymethyl)imidazolium chloride of melting point 129°–130°;

(f) from 1,3-bis(benzylideneamino)-2-(chloromethyl)-imidazolium chloride [obtained by treating 1,3-bis(benzylideneamino)-4-(hydroxymethyl)imidazolium chloride with thionyl chloride; m.p. 138°–160° (from ethanol)] there is obtained 1,3-diamino-2-(chloromethyl-)imidazolium chloride.

(g) 705 mg (4.7 mmol) of 4-dimethylaminobenzaldehyde are added to a solution of 348 mg (2.1 mmol) of 1,3-diamino-2-ethyl-imidazolium chloride in 4.4 ml of glacial acetic acid, whereupon the mixture is stirred for 20 hours. The yellow crystals obtained are filtered off and recrystallized from ethanol. There is obtained 1,3-bis[[p-(dimethyl-amino)benzylidene]amino]-2-ethylimidazolium chloride of melting point 248°.

In an analogous manner:

(h) From 1,3-diamino-2-ethylimidazolium chloride and 4-diethylaminobenzaldehyde there is obtained 1,3-bis[[p-diethylamino)benzylidene]amino]-2-ethyl-imidazolium chloride of melting point 225°–226° (from ethanol/ether);

(i) from 1,3-diamino-2-ethylimidazolium chloride and 4-dimethylamino-3,5-dimethoxy-benzaldehyde there is obtained 1,3-bis[[4-(dimethylamino)-3,5-dimethoxybenzylidene]amino]-2-ethyl-imidazolium chloride of melting point 223°–224° (from ethanol/ether);

(j) from 1,3-diamino-2-ethylimidazolium chloride and 4-amino-3,5-dimethoxy-benzaldehyde there is obtained 1,3-bis[(4-amino-3,5-dimethoxybenzylidene)amino]-2-ethyl-imidazolium chloride of melting point 226°–228° (from ethanol/ether);

(k) from 1,3-diamino-2-ethylimidazolium chloride and p-(4-methyl-1-piperazinyl)benzaldehyde there is obtained 2-ethyl-1,3-bis[[p-(4-methyl-1-piperazinyl)benzylidene]-amino]-imidazolium chloride of melting point 242° (from ethanol/ether);

(l) from 1,3-diamino-2-ethylimidazolium chloride and p-(N-morpholino)benzaldehyde there is obtained 2-ethyl-1,3-bis[(p-morpholinobenzylidene)amino]imidazolium chloride of melting point 244°–245° (from ethanol);

(m) from 1,3-diamino-2-ethylimidazolium chloride and 4-dimethylamino-1-naphthalene-carboxaldehyde there is obtained 1,3-bis[[[4-(dimethylamino)-1-naphthyl]methylidene]amino]-2-ethyl-imidazolium chloride of melting point 215° (from ethanol/ether).

(n) from 1,3-diamino-2-(hydroxymethyl)imidazolium chloride and 4-dimethylaminobenzaldehyde there is obtained 1,3-bis[[p-(dimethylamino)benzylidene]amino]-2-(hydroxymethyl)imidazolium chloride of decomposition point 265° (from methanol);

(o) from 1,3-diamino-4-methylimidazolium chloride and 4-dimethylaminobenzaldehyde there is obtained 1,3-bis[[p-(dimethylamino)benzylidene]amino]-4-methylimidazolium chloride of melting point 230°–232° (from methanol/ether);

(p) from 1,3-diamino-4-(hydroxymethyl)imidazolium chloride and 4-dimethylaminobenzaldehyde there is obtained 1,3-bis-[[p-(dimethylamino)benzylidene]amino]-4-(hydroxymethyl)-imidazolium chloride of decomposition point 243°–245° (from ethanol);

(q) from 1,3-diamino-2-(ethoxymethyl)imidazolium chloride and 4-dimethylaminobenzaldehyde there is obtained 1,3-bis-[[p-(dimethylamino)benzylidene]amino]-2-(ethoxymethyl)-imidazolium chloride of melting point 244° (from methanol);

(r) from 1,3-diamino-2-(chloromethyl)imidazolium chloride and 4-dimethylaminobenzaldehyde there is obtained 1,3-bis-[[p-(dimethylamino)benzylidene]amino]-2-(chloromethyl)-imidazolium chloride of decomposition point 242° (from methanol);

(s) from 1,3-diamino-2-ethylimidazolium chloride and 2-(dimethylamino)-5-methylbenzaldehyde there is obtained 1,3-bis[[2-(dimethylamino-5-methylbenzylidene]amino]-2-ethylimidazolium chloride of melting point 185° (from ethanol/ether).

EXAMPLE 2

(a) 1.0 g (6.2 mmol) of 1,3-diamino-2-ethyl-imidazolium chloride is placed on a column loaded with 30 g of Amberlite IR45 (acetate), whereupon elution is carried out with about 600 ml of water. The eluate is evaporated. There is obtained 1,3-diamino-2-ethyl-imidazolium acetate with an approximate melting point of 20°–25°.

(b) 1.15 g (6.2 mmol) of 1,3-diamino-2-ethyl-imidazolium acetate are dissolved in 10 ml of glacial acetic acid, whereupon the solution is treated with 1.85 g (12.4 mmol) of 4-dimethylaminobenzaldehyde. The mixture is left to stand at room temperature for 16 hours, the solution is diluted with 30 ml of ethanol and the product is precipitated by the addition of ether. After recrystallization from ethanol/ether there is obtained 1,3-bis[[(p-dimethylamino)benzylidene]amino]-2-ethylimidazolium acetate of melting point 166°–167° (decomposition).

EXAMPLE 3

1.95 g (7.4 mmol) of p-[4-(ethoxycarbonyl)-1-piperazinyl]benzaldehyde are added to a solution of 0.69 g (3.7 mmol) of 1,3-diamino-2-ethyl-imidazolium acetate in 10 ml of glacial acetic acid, the mixture is left to stand at room temperature for 18 hours, then diluted with 30 ml of ethanol and the product is crystallized out by the addition of ether. There is obtained 1,3-bis[[[p-(4-(ethoxycarbonyl)-1-piperazinyl]benzylidene]amino]-2-ethyl-imidazolium acetate diacetate of melting point 187°–188°.

EXAMPLE 4

(a) 1.5 g (9.25 mmol) of 1,3-diamino-2-ethyl-imidazolium chloride are placed on a column loaded with 30 g of Amberlite IR45 (propionate), whereupon elution is carried out with about 600 ml of water. The eluate is evaporated. There is obtained 1,3-diamino-2-ethyl-imidazolium propionate with an approximate melting point of 20°–25°.

(b) 3.88 g (18.5 mmol) of 4-dimethylamino-3,5-dimethoxybenzaldehyde are added to a solution of 1.85 g (9.25 mmol) of 1,3-diamino-2-ethyl-imidazolium propionate in 10 ml of propionic acid. The mixture is left to stand at room temperature for 16 hours and the product is crystallized out by the addition of ether and petroleum ether. After recrystallization from ether there is obtained 1,3-bis[[4-(dimethylamino)-3,5-dimethoxybenzylidene]amino]-2-ethyl-imidazolium propionate of melting point 138°–139°.

EXAMPLE 5

(a) 324 mg (2 mmol) of 1,3-diamino-2-ethyl-imidazolium chloride are placed on a column loaded with 30 g of Amberlite IR45 (citrate), whereupon elution is carried out with about 500 ml of water. After evaporation of the eluate there is obtained 1,3-diamino-2-ethyl-imidazolium citrate as a yellow oil.

(b) 910 mg (1.5 mmol) of 1,3-diamino-2-ethyl-imidazolium citrate are dissolved in 20 ml of 2-propanol, whereupon the solution is treated with 630 mg (3 mmol) of 4-di-methylamino-3,5-dimethoxybenzaldehyde, left to stand at room temperature for 2 days and the yellow solution is then concentrated. The product is crystallised out by the addition of petroleum ether. After recrystallization from ethanol/petroleum ether there is obtained 1,3-bis[[4-(dimethylamino)-3,5-dimethoxybenzylidene]amino]-2-ethyl-imidazolium citrate of melting point 140°–144°.

EXAMPLE 6

(a) 2.98 g (20 mmol) of p-dimethylaminobenzaldehyde are added to a solution of 3.24 g (20 mmol) of 1,3-diamino-2-ethylimidazolium chloride in 180 ml of glacial acetic acid. The mixture is stirred at room temperatured for 50 hours, the precipitated 1,3-bis[[p-(dimethylamino)benzylidene]amino]-2-ethylimidazolium chloride is then filtered off and washed with ethanol. The mother liquor is evaporated and the residue is placed on a column loaded with 200 g of silica gel (particle size: 0.063–0.200 mm). By elution with methylene chloride/methanol (9:1 v/v) there is obtained a further portion of 1,3-bis[[p-(dimethylamino)benzylidene]amino]-2-ethyl-imidazolium chloride.

By elution with methylene chloride/methanol (3:2 v/v) and subsequent recrystallization of the resulting material from ethanol/ether there is obtained 3-amino-1-[[p-(dimethylamino)benzylidene]amino]-2-ethylimidazolium chloride of melting point 207°–208° (decomposition).

(b) 293 mg (1 mmol) of 3-amino-1-[[p-(dimethylamino)-benzylidene]amino]-2-ethylimidazolium chloride are dissolved in 40 ml of ethanol, whereupon the solution is hydrogenated at room temperature over 50 mg of palladium (5 percent on carbon). After crystallization from ethanol/ether there is obtained 3-amino-1-[[p-(dimethylamino)benzyl]amino]-2-ethylimidazolium chloride of melting point 153°–154°.

(c) 0.5 g (3.38 mmol) of p-dimethylaminobenzaldehyde is added to a solution of 1.0 g (3.38 mmol) of 3-amino-1-[[p-(dimethylamino)benzyl]amino]-2-ethylimidazolium chloride in 15 ml of glacial acetic acid, the mixture is stirred at room temperature for 24 hours, the solution is evaporated and the crude product is chromatographed on 60 g of silica gel (particle size 0.063–0.200 mm) while eluting with methylene chloride/methanol (3:1 v/v). After recrystallizing the resulting material from ethanol/ether there is obtained 2-ethyl-1-[[p-(dimethylamino)benzyl]-amino]-3-[[p-(dimethylamino)benzylidene]amino]imidazolium chloride of melting point 201°–202°.

EXAMPLE 7

0.61 g (4 mmol) of p-nitrobenzaldehyde is added to a solution of 1.19 g (4 mmol) of 3-amino-1-[[p-(dimethylamino)benzylidene]amino]-2-ethylimidazolium chloride in 10 ml of glacial acetic acid, the mixture is stirred at room temperature for 16 hours and the product is precipitated by the addition of ether. The product is then filtered off and recrystallized from ethanol. There is obtained 1-[[p-(dimethylamino)benzylidene]amino]-2-ethyl-3-[(p-nitrobenzylidene)amino]imidazolium chloride of melting point 250°.

EXAMPLE 8

0.58 g of (4.14 mmol) of p-chlorobenzaldehyde is added to a solution of 1.0 g (4.18 mmol) of 3-amino-1-[[p-(dimethylamino)benzylidene]amino]-2-ethylimidazolium chloride in 40 ml of glacial acetic acid and the mixture is left to stand at room temperature for 24 hours. The product is then filtered off, washed with ether and recrystallized from ethanol. There is obtained 3-[p-(chlorobenzylidene)-amino]-1-[[p-(dimethylamino)benzylidene]amino]-2-ethylimidazolium chloride of melting point 246° (decomposition).

EXAMPLE 9

(a) 2.16 g (10 mmol) of 3,4,5-trimethoxybenzyl chloride are added to a solution of 1.99 g (10 mmol) of 1-benzylideneamino-2-ethylimidazole in 10 ml of acetonitrile and the mixture is heated under reflux for 28 hours. The crystallized-out product is filtered off and washed with ether. There is obtained 1-benzylideneamino-2-ethyl-3-(3,4,5-trimethoxybenzyl)imidazolium chloride of melting point 205°.

(b) 3.1 g (7.45 mmol) of 1-benzylideneamino-2-ethyl-3-(3,4,5-trimethoxybenzyl)imidazolium chloride are dissolved in 70 ml of water, whereupon the solution is treated with 8 ml of 25 percent hydrochloric acid. The resulting benzaldehyde is removed by steam distillation. After evaporation the product is recrystallized from ethanol/ether. There is obtained 1-amino-2-ethyl-3-(3,4,5-trimethoxybenzyl)-imidazolium chloride of melting point 174°.

(c) 1.9 g (5.8 mmol) of 1-amino-2-ethyl-3-(3,4,5-trimethoxybenzyl)imidazolium chloride are dissolved in 38 ml of glacial acetic acid, whereupon the solution is treated with 0.86 g (5.8 mmol) of p-dimethylaminobenzaldehyde, stirred at room temperature for 52 hours and then evaporated. The product is recrystallized from ethanol/ether. There is obtained 2-ethyl-1-[[p-(dimethylamino)benzylidene]amino]-3-(3,4,5-trimethyoxybenzyl)imidazolium chloride of melting point 211°.

EXAMPLE 10

(a) 2.23 g (10 mmol) of 4-methoxyphenacyl bromide are added to a solution of 1.99 g (10 mmol) of 1-benzylideneamino-2-ethylimidazole in 80 ml of ethylene chloride. The mixture is stirred at 60° for 3 hours, the crystallized-out product is filtered off and washed with ether. There is obtained 1-(benzylideneamino)-2-ethyl-3-(p-methoxyphenacyl)imidazolium bromide of melting point 221°-222°.

(b) A mixture of 0.86 g (2 mmol) of 1-(benzylideneamino)-2-ethyl-3-(p-methoxyphenacyl-)imidazolium bromide and 10 ml of 5 percent hydrobromic acid is heated, whereby the resulting benzaldehyde is removed by steam distillation. The product obtained after evaporation is recrystallized from ethanol/ether. There is obtained 1-amino-2-ethyl-3-(p-methoxyphenacyl)-2-ethylimidazolium bromide of melting point 213°-215°.

(c) 1.18 g (7.9 mmol) of p-dimethylaminobenzaldehyde are added to a solution of 2.7 g (7.9 mmol) of 1-amino-2-ethyl-3-(p-methoxyphenacyl)-2-ethylimidazolium bromide in 40 ml of glacial acetic acid. The mixture is stirred at room temperature for 4 days, the product is crystallized out by the addition of ether and filtered off. It is washed with water, dried at room temperature and recrystallized from ethanol. There is obtained 1-[[p-(dimethylamino)benzylidene]amino]-2-ethyl-3-(p-methoxyphenacyl)-imidazolium bromide of melting point 244°-246°.

EXAMPLE 11

(a) 1.99 g (10 mmol) of 1-(benzylideneamino)-2-ethylimidazole are added to a solution of 1.79 g (10 mmol) of 1-bromo-3,3-dimethyl-2-butanone in 30 ml of ethylene chloride and the mixture is then stirred at 60° for 5 hours. The crystallized-out product is filtered off and washed with ether. There is obtained 1-(benzylideneamino)-2-ethyl-3-(pivaloylmethyl)imidazolium bromide of melting point 219°-221°.

(b) 756 mg (2 mmol) of 1-(benzylideneamino)-2-ethyl-3-pivaloylmethyl)imidazolium bromide are subjected to a steam distillation in a mixture of 5 ml of water and 1 ml of 48 percent hydrobromic acid until benzaldehyde no longer evolves. Thereupon, the mixture is evaporated and the residue is recrystallized from ethanol/ether. There is obtained 1-amino-2-ethyl-3-(3,3-dimethyl-2-oxobutyl)-imidazolium bromide of melting point 222°-223°.

(c) 2.38 g (8.2 mmol) of 1-amino-2-ethyl-3-(3,3-dimethyl-2-oxobutyl)imidazolium bromide are dissolved in 30 ml of glacial acetic acid, whereupon the solution is treated with 1.22 g (8.2 mmol) of p-dimethylaminobenzaldehyde. After stirring at room temperature 48 hours the product is recrystallized by the addition of ether, chromatographed on 20 g of silica gel (particle size 0.063-0.200 mm) while eluting with methylene chloride/methanol (19:1 v/v) and recrystallized from ethanol/ether. There is obtained 1-[[4-(dimethylamino)benzylidene]amino]-2-ethyl-3-(pivaloylmethyl)imidazolium bromide of melting point 188°-189°.

EXAMPLE 12

(a) 2.24 g (15 mmol) of p-dimethylaminobenzaldehyde are added to a solution of 2.22 g (15 mmol) of 1-amino-2-ethylimidazole hydrochloride in 40 ml of glacial acetic acid. After leaving to stand at room temperature for 24 hours the product is crystallized out by the addition of ether and subsequently recrystallized from ethanol/ether. There is obtained 1-[[p-(dimethylamino)benzylidene]amino]-2-ethylimidazole hydrochloride of melting point 226°-228°.

In an analogous manner, using 1-amino-2-(hydroxymethyl)imidazole hydrochloride there is obtained 1-[[p-(dimethylamino)benzylidene]amino]-2-(hydroxymethyl)imidazole hydrochloride of melting point 245°-247° (from ethanol).

(b) The base is liberated from 7.3 g (26 mmol) of 1-[[p-(dimethylamino)benzylidene]amino]-2-ethylimidazole hydrochloride with saturated sodium hydrogen carbonate solution. This base is taken up in methylene chloride. The solution is dried over sodium sulphate and concentrated. There is obtained 1-[[p-(dimethylamino)benzylidene]amino]-2-ethylimidazole of melting point 120°-121°.

In an analogous manner, from 1-[[p-(dimethylamino)benzylidene]amino]-2-(hydroxymethyl)imidazole hydrochloride with sodium carbonate solution there is obtained 1-[[p-(dimethylamino)benzylidene]amino]-2-(hydroxymethyl)-imidazole of melting point 205°-207°.

(c) 1.82 g (7.5 mmol) of 1-[[p-(dimethylamino)benzylidene]amino]-2-ethylimidazole are dissolved in 50 ml of ethylene chloride, whereupon the solution is treated with 1.95 g (10 mmol) of t-butyl bromoacetate. After leaving to stand at room temperature for 18 hours the solution is concentrated and the residue is recrystallized from ethanol/ether. There is obtained 3-[(t-butoxycarbonyl)-methyl]-1-p-[[(dimethylamino)benzylidene]amino]-2-ethylimidazolium bromide of melting point 192° (decomposition).

(d) In an analogous manner from 1-[[p-(dimethylamino)benzylidene]amino]-2-(hydroxymethyl)imidazole there is obtained 3-[(t-butoxycarbonyl)methyl]-1-p-[[(dimethylamino)benzylidene]amino]-2-(hydroxymethyl)-imidazolium bromide of melting point 195°–196° (from water).

EXAMPLE 13

(a) 1.44 g (6 mmol) of 1-[[p-(dimethylamino)benzylidene]-amino]-2-ethylimidazole are dissolved in 20 ml of methylene chloride. The solution is treated with 1.72 g (6 mmol) of 3,4,5-trimethoxyphenacyl bromide and left to stand at room temperature for 46 hours. The product is crystallized out by the addition of ether and recrystallized from ethanol. There is obtained 1-[[p-(dimethylamino)benzylidene]amino]-2-ethyl-3-(3,4,5-trimethoxyphenacyl)-imidazolium bromide of melting point 232° (decomposition).

(b) In an analogous manner, from 1-[[p-(dimethylamino)benzylidene]amino]-2-isopropylimidazole and 1-bromo-pinacolone there is obtained 3-[[p-(dimethylamino)benzylidene]-amino]-2-isopropyl-1-(pivaloylmethyl)imidazolium bromide of melting point 236°–237° (dec.; from acetonitrile/ether).

EXAMPLE 14

A solution of 2.42 g (10 mmol) of 1-[[p-(dimethylamino)benzylidene]amino]-2-ethylimidazole is treated with 2.42 g (10 mmol) of p-dimethylaminophenacyl bromide. After stirring at 40° for 30 minutes the product is crystallized out by the addition of ether and recrystallized from methylene chloride/ether. There is obtained 3-[p-(dimethylamino)phenacyl]-1-[[p-(dimethylamino)benzylidene]-amino]-2-ethylimidazolium bromide of melting point 247°.

EXAMPLE 15

(a) 25 g (0.23 mmol) of 2-propylimidazole are suspended in 70 ml of water, whereupon the suspension is treated within 20 minutes while stirring with a solution, prepared at 0°, of 25 g (0.22 mmol) of hydroxylamine O-sulphonic acid and 18.5 g (0.22 mmol) of sodium hydrogen carbonate in 150 mol of water. After stirring at room temperature for 20 hours the mixture is acidified with 65 ml of 2N hydrochloric acid, a solution of 15.5 g (0.15 mol) of benzaldehyde in 50 ml of ether is added thereto and the mixture is stirred at room temperature for 6 hours. White crystals form and these are filtered off and dissolved in methylene chloride. The mother liquor is processed further as described below. The solution is dried over sodium sulphate and concentrated, whereupon the residue is crystallized out by the addition of ether. After recrystallization from ethanol there is obtained 1,3-bis[[benzylidene]amino]-2-propyl-immidazoliumbenzaldoxime O-sulphonate of melting point 143°–145°.

(b) The above mother liquor is washed with ether, treated with 60 ml of 3N sodium hydroxide solution and extracted with methylene chloride. After drying the extract over sodium sulphate there is obtained a reddish oil which is chromatographed on silica gel (particle size 0.063–0.2 mm) while eluting with methylene chloride/methanol (99:1 v/v). There is obtained 1-(benzylidene)amino-2-propyl-imidazole of melting point 61°–62°.

(c) In an analogous manner, from 2-butylimidazole, hydroxylamine O-sulphonic acid and benzaldehyde there is obtained 1,3-bis[[benzylidene]amino]-2-butyl-imidazolium benazldoxime O-sulphonate of melting point 137°–140° (not recrystallized) and (d) 1-(benzylidene)amino-2-butyl-imidazole of melting point 60°–61° (from pentane).

(e) 18.6 g (36 mmol) of 1,3-bis[[benzylidene]amino]-2-propyl-imidazolium-benzaldoxime O-sulphate are suspended in 100 ml of water and 70 ml of 2N hydrochloric acid and subjected to a steam distillation on a steam-bath until benzaldehyde no longer evolves. The solution is evaporated and the residue is crystallized from ethanol/ether. The crude product is placed on a column loaded with 200 ml of ion exchanger Amberlite IRA 400 (chloride), whereupon elution is carried out with water. The eluate is evaporated and the residue is recrystallized from ethanol/ether. There is obtained 1,3-diamino-2-propyl-imidazolium chloride of melting point 197°–199°.

(f) In an analogous manner, from 1,3-bis[[benzylidene]-amino]-2-butyl-imidazoliumbenzaldoxime O-sulphonate there is obtained 1,3-diamino-2-butyl-imidazolium chloride of melting point 146°–147° (from ethanol/ether).

(g) 1.49 g (10 mmol) of 4-dimethylamino-benzaldehyde are added to a solution of 0.88 g (5 mmol) of 1,3-diamino-2-propyl-imidazolium chloride in 15 ml of glacial acetic acid. After leaving to stand at room temperature for 2 days the product is crystallized out by the addition of ether and then recrystallized from ethanol. There is obtained 1,3-bis[[p-(dimethylamino)benzylidene]amino]-2-propyl-imidazolium chloride of melting point 252°.

In an analogous manner:

(h) From 1,3-diamino-2-butyl-imidazolium chloride and 4-dimethylamino-benzaldehyde there is obtained 2-butyl-1,3-bis[[p-(dimethylamino)benzylidene]amino]imidazolium chloride of melting point 240° (from ethanol) (decomposition);

(i) from 1,3-diamino-2-isopropylimidazolium chloride there is obtained 1,3-bis[[p-(dimethylamino)benzylidene]amino]-2-isopropylimidazolium chloride of melting point 241°.

EXAMPLE 16

1.43 g (6.8 mmol) of 4-dimethylamino-3,5-dimethoxybenzaldehyde are added to a solution of 0.60 g (3.4 mmol) of 1,3-diamino-2-propyl-imidazolium chloride in 5 ml of glacial acetic acid. After leaving to stand for 16 hours the product is crystallized out by the addition of ether and then recrystallized from ethanol. There is obtained 1,3-bis[[4-(dimethylamino)-3,5-dimethoxybenzylidene]amino]-2-propylimidazolium chloride of melting point 218°–219°.

EXAMPLE 17

(a) A solution, prepared at 0°, of 10 g (88 mmol) of hydroxylamine O-sulphonic acid and 7.4 g (88 mmol) of sodium hydrogen carbonate in 60 ml of water is added dropwise to a solution of 7.26 g (88 mmol) of 2-methylimidazole in 30 ml of water. In so doing the temperature rises to 35°. After stirring for 16 hours the mixture is acidified with 26 ml of 2N hydrochloric acid. A solution of 6.26 g (59 mmol) of benzaldehyde in 20 ml of ether is added thereto, whereupon the mixture is stirred for a further 6 hours. The precipitated product is filtered off and recrystallized from methanol/ether. There is obtained 1,3-bis(benzylideneamino)-2-methylimidazoliumbenzaldoxime O-sulphonate of melting point 249°–250°.

(b) 19.2 g (39 mmol) of 1,3-bis(benzylideneamino)-2-methylimidazoliumbenzaldoxime O-sulphonate are subjected to a steam distillation in 100 ml of water and 70 ml of 2N hydrochloric acid until benzaldehyde no longer results. The mixture is evaporated and the residue is placed on a column loaded with 200 ml of ion exchanger Amberlite IRA 400 (chloride). Elution is carried out with about 1 liter of water, the eluate is evaporated and the material obtained is recrystallized from ethanol/methylene chloride. There is obtained 1,3-diamino-2-methyl-imidazolium chloride of melting point 225°–227°.

(c) 1.0 g (6.76 mmol) of 1,3-diamino-2-methylimidazolium chloride is placed on a column loaded with 30 g of Amberlite IR 45 (acetate), whereupon elution is carried out with water. After evaporation of the solution there is obtained 1,3-diamino-2-methylimidazolium acetate as a viscous oil which solidifies gradually.

(d) 1.9 g (12.8 mmol) of 4-dimethylamino-benzaldehyde are added to a solution of 1.1 g (6.4 mmol) of 1,3-diamino-2-methylimidazolium acetate in 11 ml of glacial acetic acid. After leaving to stand at room temperature for 16 hours 50 ml of ethanol are added and the product is crystallized out by the addition of ether. After recrystallization from ethanol/ether there is obtained 1,3-bis[[(p-dimethylamino)benzylidene]amino]-2-methylimidazolium acetate of melting point 166°–167° (decomposition).

In an analogous manner:

(e) Using 4-pyrrolidinobenzaldehyde there is obtained 1,3-bis[[4-pyrrolidinobenzylidene]amino]-2-methylimidazolium chloride of melting point 258° (from ethanol/ether);

(f) using 3-(dimethylamino)-5-phenylbenzaldehyde there is obtained, after chromatography on silica gel with n-butanol/water/ethyl acetate (4:1:1), 1,3-bis[[2-(dimethylamino)-5-phenylbenzylidene]amino]-2-methylimidazolium chloride hydrochloride of melting point 268°–270° (from ethanolic hydrochloric acid);

(g) using 5-(dimethylamino)-2-thiophenecarboxaldehyde there is obtained, after chromatography on silica gel with n-butanol/water/acetic acid (4:1:1), 1,3-bis[[5-(dimethylamino)-2-thienylmethylene]amino]-2-methylimidazolium chloride of melting point 260°–262° (from ethanol).

EXAMPLE 18

(a) 1.61 g (10 mmol) of p-chlorobenzyl chloride are added to a solution of 1.99 g (10 mmol) of 1-(benzylidene)amino-2-ethylimidazole in 10 ml of acetonitrile. After heating under reflux for 24 hours the precipitated product is filtered off and recrystallized from ethanol/ether. There is obtained 1-(benzylideneamino)-3-(p-chlorobenzyl)-2-ethylimidazolium chloride of melting point >200°.

(b) 500 mg (1.39 mmol) of 1-(benzylideneamino)-3-(p-chlorobenzyl)-2-ethylimidazolium chloride are subjected to a steam distillation in 5 ml of water and 2 ml of 3N hydrochloric acid until benzaldehyde no longer evolves. The mixture is evaporated and the residue is recrystallized from ethanol/ether. There is obtained 1-amino-3-(p-chlorobenzyl)-2-ethylimidazolium chloride of melting point 223°–225°.

(c) 2.44 g (9 mmol) of 2-(p-chlorobenzyl)-2-ethylimidazolium chloride are dissolved in 25 ml of glacial acetic acid, whereupon the solution is treated with 1.34 g (9 mmol) of 4-dimethylaminobenzaldehyde. After stirring room temperature for 24 hours the product is crystallized out by the addition of ether and is recrystallized from ethanol/ether. There is obtained 3-(p-chlorobenzyl)-1-[[p-(dimethylamino)benzylidene]amino]-2-ethylimidazolium chloride of melting point 79°–81°.

EXAMPLE 19

(a) 2.33 g (10 mmol) of p-chlorophenacyl bromide are added to a solution of 1.99 g (10 mmol) of 1-(benzylidene)amino-2-ethylimidazole in 30 ml of ethylene chloride. After stirring at 60° for 2 hours the product is filtered off and washed with ether. There is obtained 1-(benzylideneamino)-3-(p-chlorophenacyl)-2-ethylimidazolium bromide of melting point 236°–237°.

(b) 864 mg (2 mmol) of 1-(benzylideneamino)-3-(p-chlorophenacyl)-2-ethylimidazolium bromide are subjected to a steam distillation in 5 ml of water and 2 ml of 48 percent hydrobromic acid until benzaldehyde no longer evolves. The solution is concentrated and te precipitated product is filtered off. There is obtained 1-amino-3-(p-chlorophenacyl)-2-ethylimidazolium bromide of melting point 209°–210°.

(c) A suspension consisting of 1.72 g (5 mmol) of 1-amino-3-(p-chlorophenacyl)-2-ethylimidazolium bromide and 0.74 g (5 mmol) of 4-dimethylaminobenzaldehyde in 15 ml of glacial acetic acid is stirred at room temperature for 48 hours, treated with ether and filtered. The filtered-off crude product is chromatographed on 30 g of silica gel (particle size 0.063–0.200 mm) while eluting with methylene chloride/methanol (9:1 v/v) and then recrystallized from methylene chloride/methanol/ether. There is obtained 3-(p-chlorophenacyl)-1-[[p-(dimethylamino)benzylidene]amino]-2-ethylimidazolium bromide of melting point 252°–253°.

EXAMPLE 20

2.2 g of 1,3-diamino-2-methylimidazolium chloride and 6.9 g of 4-dimethylamino-3,5-dimethoxy-benzaldehyde are dissolved in 100 ml of glacial acetic acid, whereupon the solution is stirred at room temperature for 48 hours. The glacial acetic acid is distilled off in vacuo and the residue is dissolved in 100 ml of ethyl acetate. After crystallization sets in a further 300 ml of ethyl acetate are added thereto, whereupon the mixture is cooled to 10°. The crystallized-out material is filtered off under suction, washed with 100 ml of ethyl acetate and dried over potassium hydroxide in vacuo at 80°. There is obtained 1,3-bis[[4-(dimethylamino)-3,5-dimethoxybenzylidene]amino]-2-methylimidazolium chloride of decomposition point 226°.

EXAMPLE 21

(a) 1.3 g (10 mmol) of 1-amino-2-methylimidazole hydrochloride and 2.2 g (15 mmol) of p-dimethylaminobenzaldehyde are stirred at room temperature in 100 ml of glacial acetic acid for 16 hours. The mixture is evaporated, whereupon the residue is treated four times with ethanol and evaporated each time. The crystalline residue is washed with ether and then treated with saturated sodium hydrogen carbonate solution. The mixture is extracted with methylene chloride, the extract is dried over sodium sulphate, evaporated and the material obtained is recrystallized from methylene chloride/petroleum ether. There is obtained 1-[[p-(dimethylamino)benzylidene]amino]-2-methylimidazole of melting point 166°–167°.

(b) 228 mg (1 mmol) of 1-[[p-(dimethylamino)benzylidene]-amino]-2-methylimidazole are dissolved in 20 ml of methylene chloride (in a further experiment methylene chloride/ethanol was used as the solvent), whereupon the solution is treated portionwise with 446 mg (2 mmol) of o-diphenylphospinylhydroxylamine within 2 weeks while stirring. The mixture is evaporated; the residue is taken up in 200 ml of water and placed on a column loaded with 10 ml of ion exchanger Amberlite IRA 400 (chloride). Elution is carried out with water, the eluate is evaporated and the material obtained is chromatographed on 20 g of silical gel (particle size 0.063–0.2 mm) with methylene chloride/methanol (7:3 v/v). By recrystallization from ethanol/ether there is obtained 1-amino-3-[[p-(dimethylamino)-benzylidene]-amino]-2-methylimidazolium chloride of melting point 230°–231°.

(c) 56 mg (0.2 mmol) of 1-amino-3-[[p-(dimethylamino)-benzylidene]amino]-2-methylimidazolium chloride and 30 mg (0.2 mmol) of p-nitrobenzaldehyde are dissolved in 5 ml of glacial acetic acid. After 2 days the solution is evaporated, and the residue is chromatographed on 5 g of silica gel (particle size 0.063–0.200 mm) while eluting chloroform/methanol (87:13) and recrystallized from methylene chloride/petroleum ether. There is obtained 1-[[p-(dimethylamino)benzylidene]amino]-2-methyl-3-[[p-nitrobenzylidene]amino]-imidazolium chloride of melting point 252° (decomposition).

EXAMPLE 22

(a) 7.92 g (171 mmol) of sodium hydride (55–60 percent dispersion in oil) are washed with absolute tetrahydrofuran. A solution of 13.2 g (83 mmol) of 2-methyl-4-phenylimidazole in 356 ml of N-methylpyrrolidone is added dropwise at 0°. The mixture is subsequently stirred at room temperature until the evolution of gas is no longer observed. 39.6 g (171 mmol) of O-diphenylphosphinylhydroxylamine are added portionwise thereto and the mixture is stirred for a further 18 hours. 400 ml of water are added thereto. The mixture is stirred for 1 hour and extracted four times with 1300 ml of methylene chloride each time. The extract is dried over sodium sulphate and evaporated. The residue is place on a column loaded with 700 g of silica gel (particle size 0.063–0.200 mm) amnd the product is eluted with methylene chloride/ethanol (98:2). The oil (N-amino-2-methyl-4-phenylimidazole) obtained after concentration is dissolved with 1150 ml of methylene chloride and treated with 13.94 g (60 mmol) of O-diphenylphosphinylhydroxylamine. After stirring for 3 days a further 13.94 g (60 mmol) of O-diphenylphosphinylhydroxylamine are added thereto and the mixture is stirred for a further 24 hours. The mixture is concentrated and the residue is placed on a column loaded with Amberlite IRA 400 (chloride). Elution is carried out with water. The aqueous solution is evaporated and the residue is placed on a column loaded with 300 g of silica gel (particle size 0.063–0.200 mm). The product is eluted with methylene chloride/ethanol (1:9). From the eluate there is obtained 1,3-diamino-2-methyl-4-phenylimidazolium chloride of melting point 162°–163°.

(b) 3.6 g (16 mmol) of the chloride are dissolved in 60 ml of glacial acetic acid. 4.78 g (32 mmol) of p-dimethylaminobenzaldehyde are added thereto. After stirring for 20 hours 10 ml of ether are added thereto and the mixture is stirred for a further 24 hours. The mixture is concentrated and the residue is placed on a column loaded with 280 g of silica gel (particle size 0.063–0.200 mm). The product is eluted with methylene chloride and crystallized from ethanol/ether. There is obtained 1,3-bis[[p-(dimethylamino)benzylidene]amino]-2-methyl-4-phenylimidazolium chloride of melting point 254°.

In an analogous manner there are obtained:
(c) 1,3-Bis[[p-(dimethylamino)benzylidene]amino]-2-ethyl-4-methyl-imidazolium chloride of melting point 218°–219°;
(d) 1,3-bis[[p-(dimethylamino)benzylidene]amino]-2-ethylbenzimidazolium chloride of melting point 152°–153°.

EXAMPLE 23

(a) 86.0 g (767 mmol) of 4-hydroxymethyl-2-methylimidazole are dissolved in 240 ml of water. A freshly prepared solution of 89.35 g (790 mmol) of hydroxylamine O-sulphonic acid and 66.4 g (790 mmol) of sodium bicarbonate in 390 ml of water is added dropwise thereto within 15 minutes. The mixture is stirred at room temperature for 20 hours. The mixture is acidified with 200 ml of 2N hydrochloric acid and 55.4 g (522 mmol) of benzaldehyde dissolved in 280 ml of ether are added thereto. The mixture is stirred for 6 hours, the precipitated product is filtered off, washed with water and ether and dried at 40° in a high vacuum. There is obtained 1,3-bis[[benzylidene]amino]-4-hydroxymethyl-2-methylimidazoliumbenzaldoximide O-sulphonate of melting point 161°–163° (crude product).

(b) This product is suspended in 200 ml of water and 100 ml of 3N hydrochloric acid and the suspension is subjected to a steam distillation on a steam-bath until benzaldehyde no longer evolves. The solution is evaporated and the residue is placed on a column loaded with 100 ml of ion exchanger Amberlite IRA 400 (chloride), whereupon elution is carried out with water. The eluate is evaporated and the residue is crystallized from ethanol/ether. There is obtained 1,3-diamino-4-(hydroxymethyl)-2-methylimidazolium chloride of melting point 129°–130°. A further portion of melting point 125°–126° is obtained from the mother liquor.

(c) 0.89 g (5 mmol) of 1,3-diamino-4-(hydroxymethyl)-2-methylimidazolium chloride and 1.49 g (10 mmol) of 4-dimethylaminobenzaldehyde are dissolved in 20 ml of glacial acetic acid. After 22 hours the precipitated product is filtered off and recrystallized from ethanol. There is obtained 1,3-bis[[p-(dimethylamino)benzylidene]amino]-4-(hydroxymethyl)-2-methylimidazolium chloride of melting point 237° (dec.).

EXAMPLE 24

(a) 3.8 g (21.3 mmol) of 1,3-diamino-4-(hydroxymethyl)-2-methylimidazolium chloride are taken up in 200 ml of dichloromethane and treated with 2.56 g (21.3 mmol) of thionyl chloride. The mixture is stirred at room temperature for 3 days, the product is filtered off, washed with dichloromethane and dried at 40° in a high vacuum. There is obtained 1,3-diamino-4-(chloromethyl)-2-methylimidazolium chloride of melting point 163°–165°.

(b) 0.985 g (5 mmol) of 1,3-diamino-4-(chloromethyl)-2-methylimidazolium chloride and 7.45 g (50 mmol) of 4-dimethylaminobenzaldehyde are dissolved in 250 ml of glacial acetic acid. The solution is left to stand at room temperature for 36 hours and evaporated. The residue is placed on a column loaded with 150 g of silica gel (particle size 0.063–0.2 mm) and the product is eluted with chloroform/methanol (9:1). The eluate is evaporated and the product is crystallized from ethanol/ether. There is obtained 1,3-bis[[p-(dimethylamino)benzylidene]amino]-4-(chloromethyl)-2- methylimidazolium chloride of melting point 188° (dec.)

EXAMPLE 25

(a) A solution of 3.24 g (20 mmol) of 1,3-diamino-2-ethylimidazolium chloride and 16.5 g (100 mmol) of p-nitroacetophenone in 150 ml of glacial acetic acid is left to stand for 2 days, concentrated and the residue is crystallized from ethanol/ether. The crystals are placed on a column loaded with 50 g of silica gel. The material eluted with methylene chloride/methanol (7:3) is recrystallized from ethanol. There is obtained 1-amino-2-ethyl-3-[(α-methyl-p-nitrobenzylidene)amino]-imidazolium chloride of melting point 201°–203°.

(b) A solution of 1.15 g (3.7 mmol) of 1-amino-2-ethyl-3-[(α-methyl-p-nitrobenzylidene)amino]-imidazolium chloride and 0.55 g (3.7 mmol) of p-dimethylaminobenzaldehyde in 25 ml of glacial acetic acid is stirred for 18 hours. The product is crystallized out by the addition of ether. The product is recrystallized from ethanol/ether. There is obtained 3-[[p-(dimethylamino)-benzylidene]amino]-2-ethyl-1-[(α-methyl-p-nitrobenzylidene)amino]-imidazolium chloride of melting point 233°.

EXAMPLE 26

(a) 380 mg (2 mmol) of triethyloxonium tetrafluoroborate are dissolved in 15 ml of methylene chloride. 326 mg (2 mmol) of p-dimethylaminoacetophenone are added thereto at −15°. After 5 minutes there are added thereto at the same temperature 162 mg (1 mmol) of 1,3-diamino-2-ethyl-imidazolium chloride and the mixture is stirred at −10° for 1 hour and at 0° for 2 hours. After the addition of a small amount of methanol the mixture is evaporated and the residue is placed on a column loaded with 10 g of silica gel. The product is eluted with chloroform/methanol (87:13 parts by weight) and crystallized using ether. The crystallizate is dissolved in 80 ml of water, placed on a column loaded with ion exchanger Amberlite IRA 400 (chloride) and elution is carried out with water. The eluate is evaporated and the residue is crystallized from ethanol/water. There is obtained 3-amino-1-[[p-(dimethylamino)-α-methylbenzylidene]amino]-2-ethylimidazolium chloride of melting point 223°–225°.

(b) 435 mg (1.41 mmol) of 3-amino-1-[[p-dimethylamino)-α-methylbenzylidene]amino]-2-ethylimidazolium chloride and 210 mg (1.41 mmol) of p-dimethylaminobenzaldehyde are dissolved in 30 ml of glacial acetic acid. After 2 days the solution is evaporated and the residue is placed on a column loaded with 50 g of silica gel. The product is eluted with dichloromethane/methanol (9:1) and crystallized from ethanol/ether. There is obtained 3-[[p-(dimethylamino)-benzylidene]amino]-1-[[p-(dimethylamino)-α-methylbenzylidene]amino]-2-ethylimidazolium chloride of melting point >202° (decomposition).

EXAMPLE A 1,3-Bis[[(p-dimethylamino)benzylidene]amino]-2-ethyl-imidazolium acetate is used in a manner known per se as the active substance for the manufacture of tablets of the following composition:

|                  | mg/tablet |
| ---------------- | --------- |
| Active substance | 100       |
| Lactose          | 192       |
| Maize starch     | 80        |
| Hydrolyzed maize starch | 20  |
| Calcium stearate | 8         |
| Tablet weight    | 400 mg    |

What is claimed is:
1. A compound of the formula

$$\begin{array}{c} R^1 \\ \diagdown \\ R^2 \end{array} N-Q-CR^6=N-N \underset{R^3}{\overset{R^5}{\diagup\!\!\!\diagdown}} N-R^4 \quad Y^-$$

wherein Q is a mono or bicyclic carbocyclic aromatic group with two free valencies, or a mono or biheterocyclic aromatic group with two free valencies;

—NR$^1$R$^2$ is a basic amino group wherein R$^1$ is hydrogen or lower alkyl and R$^2$ is hydrogen or a saturated or unsaturated lower hydrocarbon group or R$^1$ or R$^2$ together with the nitrogen atom is a substituted or unsubstituted 5 to 7 membered saturated N-heterocycle with the substituents selected from the group consisting of one or two lower alkyl groups and which can contain as a ring member in place of one methylene group an oxygen or sulphur atom or the group >SO, >SO$_2$, >CO, >CH—Rd, or >N—Re wherein Rd is hydroxy, lower alkanoyl, lower alkoxycarbonyl, carbamoyl, mono or di(lower alkyl), carbamoyl or a saturated or partially unsaturated lower hydrocarbon group which may contain one or two oxygen atoms in ethereal and/or alcoholic form R$^3$ is hydrogen, lower alkyl, lower hydroxyalkyl, lower alkoxyalkyl or lower haloalkyl;

R$^4$ is a basic amino group as defined above or the group —N=CRc—Ra, —(NH)$_n$—CH(Rc)—Ra$^1$, —NH—CO—Rb, —CH$_2$—CO—Rb or —N=C-R$^6$—Q—NR'R$^2$;

R$^5$ is hydrogen, lower alkyl, lower hydroxyalkyl, lower alkoxy alkyl, lower haloalkyl, a mono- or bicyclic carbocyclic aromatic group or is together with the atoms in the 4- and 5-positions of the imidazole ring a benzene ring, R$^6$ is hydrogen or lower alkyl;

Ra is a mono- or bicyclic carbocyclic aromatic group, a mono- or biheterocyclic aromatic group; or a basic amino group as defined above;

Ra$^1$ is a mono- or bicyclic carbocyclic aromatic group or a mono- or biheterocyclic aromatic group;

Rb is hydrogen, Q$^1$, —OQ$^1$, or a mono- or bicyclic carbocyclic aromatic group, a mono- or biheterocyclic aromatic group, or a basic amino group as defined above which may be attached via a lower alkyl group;

Rc is hydrogen or lower alkyl;

n is 0 or 1;

the dotted line is an additional double bond;

Q$^1$ is a saturated or partially unsaturated lower hydrocarbon which may contain one or two oxygen atoms in ethereal and/or alcoholic form;

Y$^-$ is a pharmaceutically acceptable anion;

with the proviso that $R^3$ is other than hydrogen or methyl when $R^4$ is $-N=CH-Q-NR^1R^2$, $R^1$ and $R^2$ are each methyl, $R^5$ and $R^6$ are each hydrogen, Q is 1,4-phenylene and Y is chlorine or a pharmaceutically acceptable acid addition salt thereof.

2. The compound of claim 1 wherein $R^3$ is hydrogen or lower alkyl; $R^4$ is $-N=CH-Ra$, $-(NH)_n-CH_2Ra^1$, $-NH-CO-Rb$ or $-CH_2-CO-Rb$; and $R^5$ and $R^6$ are ach hydrogen.

3. The compound of claim 1, wherein $R^4$ is $-N=CR^6-Q-NR^1R^2$.

4. The compound of claim 3 wherein Q is a substituted or unsubstituted 1,4-phenylene or 1,4-naphthylene, wherein the substituents are selected from the group consisting of one or two lower alkyl lower alkoxy.

5. The compound of claim 4, wherein Q is 1,4-phenylene.

6. The compound of claim 1, wherein $R^1$ and $R^2$ are each hydrogen or lower alkyl or together with the nitrogen atom are a substituted or unsubstituted 4-morpholinyl, 1-piperazinyl, 4-(lower alkyl)-1-piperazinyl, 4-(lower alkoxycarbonyl)-1-piperazinyl or 1-pyrrolidinyl with the substituents selected from the group consisting of one or two lower alkyl.

7. The compound of claim 6, wherein $R^1$ and $R^2$ are lower alkyl.

8. The compound of claim 1, wherein $R^3$ is lower alkyl.

9. The compound of claim 1, wherein $R^4$ is $-N=C-Rc-Ra$ or $-CH_2-CO-Rb$; Ra is a substituted or unsubstituted phenyl with the substituents selected from the group consisting of one or two lower alkyl, lower alkoxy, lower alkylthio, lower alkanoyl, lower alkoxycarbonyl, halogen, trifluoromethyl, hydroxy, nitro or cyano; and Rb is a substituted or unsubstituted lower alkyl, lower alkoxy or phenyl with the substituents selected from the group consisting of one or two lower alkyl, lower alkoxy, lower alkylthio, lower alkanoyl, lower alkoxycarbonyl, halogen, trifluoromethyl, hydroxy, nitro or cyano.

10. The compound of claim 1, wherein $R^5$ is hydrogen.

11. The compound of claim 1, wherein $R^6$ and Rc are hydrogen.

12. The compound of claim 1 which is 3-[p-(Chlorobenzylidene)amino]-1-[[p-(dimethylamino)benzylidene]amino]-2-ethylimidazolium chloride.

13. The compound of claim 1 which is 3-[p-(Dimethylamino)phenacyl]-1-[[p-(dimethylamino)benzylidene]amino]-2-ethylimidazolium chloride.

14. The compound of claim 1 which is 1,3-Bis[(p-(dimethylamino)benzylidene]amino-2-ethylimidazolium chloride.

15. The compound of claim 1 which is 1-[[p-(Dimethylamino)benzylidene]amino]-2-ethyl-3-[(p-nitrobenzylidene)amino]imidazolium chloride.

16. The compound of claim 1 which is 1,3-Bis[[p-(dimethylamino)benzylidene]amino]-2-propylimidazolium chloride.

17. A compound of the formula

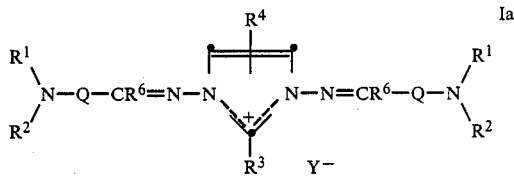

wherein Q is substituted or unsubstituted 1,4-phenylene or 1,4-naphthylene with the substituents selected from the group consisting of one or two lower alkyl or lower alkoxy; $R^1$ and $R^2$ are each independently hydrogen or lower alkyl or $R^1$ and $R^2$ taken together with the adjacent nitrogen atom are substituted or unsubstituted 4-morpholinyl, 1-piperazinyl, 4-(lower alkyl)-1-piperazinyl, 4-(lower alkoxy carbonyl)-1-piperazinyl or 1-pyrrolidinyl with the substituents selected from the group consisting of one or two lower alkyl groups; $R^3$ is hydrogen, lower alkyl, lower hydroxyalkyl, lower alkoxyalkyl or lower haloalkyl; $R^5$ is hydrogen, lower alkyl, lower hydroxyalkyl, lower alkoxyalkyl, lower haloalkyl, a mono- or bicyclic carbocyclic aromatic group or is together with the atoms in the 4- and 5-positions at the imidazole ring a benzene ring; $R^6$ is hydrogen or lower alkyl; the dotted line is an additional double bond; $Y^-$ is a pharmaceutically acceptable anion, provided that $R^3$ may not equal hydrogen or methyl when Q is equal to 1,4-phenylene, $R^1$ and $R^2$ are equal to methyl, $R^5$ and $R^6$ are equal to hydrogen and $Y^-$ is equal to Cl; or a pharmaceutically acceptable acid addition salt thereof.

18. The compound of claim 17 wherein Q is 1,4-phenylene.

19. The compound of claim 18 wherein $R^1$ and $R^2$ are lower alkyl.

20. The compound of claim 19 wherein $R^3$ is lower alkyl; $R^5$ is hydrogen; and $R^6$ is hydrogen.

21. The compound of claim 17 which is selected from the group consisting of 1,3-Bis[[p-(dimethylamino)-benzylidene]amino]-2-ethylimidazolium chloride and 1,3-Bis[[p-(dimethylamino)benzylidene]amino]-2-propylimidazolium chloride.

22. An antibacterial, antimycotic, antiprotozoacidal, or antihelminthic composition containing a pharmacologically effective amount of an imidazolium compound or a pharmaceutically acceptable acid addition salt thereof and an inert carrier material wherein said compound has the formula $$\begin{array}{c} R^1 \\ \diagdown \\ R^2 \end{array} N-Q-CR^6=N-N \underset{\underset{R^3}{|}}{\diagup\diagdown} N-R^4 \quad Y^- \qquad I$$

wherein Q is a mono or bicyclic carbocyclic aromatic group with two free valencies, or a mono or biheterocyclic aromatic group; $-NR^1R^2$ is a basic amino group wherein $R^1$ is hydrogen or lower alkyl and $R^2$ is hydrogen or a saturated or unsaturated lower hydrocarbon group or $R^1$ and $R^2$ together with the nitrogen atom is a substituted or unsubstituted 5 to 7 membered saturated N-heterocycle with the substituents selected from the group consisting of one or two lower alkyl groups and which can contain as a ring member in place of one methylene group an oxygen or sulphur atom or the group >SO, >SO$_2$, >CO, >CH—Rd, or >N—Re wherein Rd is hydroxy, lower alkanoyl, lower alkoxycarbonyl, carbamoyl, mono or di(lower alkyl) carbamoyl or a saturated or partially unsaturated lower hydrocarbon group which may contain one or two oxygen atoms in ethereal and/or alcoholic form; $R^3$ is hydrogen, lower alkyl, lower hydroxyalkyl, lower alkoxyalkyl or lower haloalkyl; $R^4$ is a basic amino group as defined above or the group —N=CRc—Ra, —(NH-)$_n$—CH(Rc)—Ra$^1$, —NH—CO—Rb, —CH$_2$—CO—Rb or —N=CR$^6$—Q—NR$^1$R$^2$; $R^5$ is hydrogen, lower alkyl, lower hydroxyalkyl, lower alkoxyalkyl, lower haloalkyl, a monobicyclic carbocyclic aromatic group or is together with the atoms in the 4- and 5-positions at the imidazole ring a benzene ring; $R^6$ is hydrogen or lower alkyl; Ra is a mono- or bicyclic carbocyclic aromatic group, a mono- or biheterocyclic aromatic group or a basic amino group as defined above; Ra$^1$ is a mono- or bicyclic carbocyclic aromatic group or; Rb is hydrogen, —Q', —OQ' or a mono- or bicyclic carbocyclic aromatic group, a mono- or biheterocyclic aromatic group, or basic amino group defined as above which may be attached via a lower alkyl group; Rc is hydrogen or lower alkyl; n is 0 or 1; the dotted line is an additional double bond; Q' is a saturated or partially unsaturated lower hydrocarbon which may contain one or two oxygen atoms in ethereal and/or alcoholic form; and the symbol Y$^-$ is a pharmaceutically acceptable anion.

23. The composition of claim 22, wherein $R^3$ is hydrogen or lower alkyl; $R^4$ is —N=CH—Ra, —(NH-)$_n$—CH$_2$—Ra', —NH—CO—Rb or —CH$_2$—CO—Rb; and $R^5$ and $R^6$ are each hydrogen.

24. The composition of claim 22, wherein $R^4$ is —N=CR$^6$—Q—NR$^1$R$^2$.

25. The composition of claim 24, wherein Q is substituted or unsubstituted 1,4-phenylene or 1,4-naphthylene, wherein the substituents are selected from the group consisting of one or two lower alkyl and lower alkoxy.

26. The composition of claim 25, wherein Q is 1,4-phenylene.

27. The composition of claim 22, wherein $R^1$ and $R^2$ are each hydrogen or lower alkyl or together with the nitrogen atom are substituted or unsubstituted 4-morpholinyl, 1-piperazinyl, 4-(lower alkyl)-1-piperazinyl, 4-(lower alkoxycarbonyl)-1-piperazinyl or 1-pyrrolidinyl with the substituents selected from the group consisting of one or two lower alkyl groups.

28. The composition of claim 27, wherein $R^1$ and $R^2$ are each lower alkyl.

29. The composition of claim 22, wherein $R^3$ is lower alkyl.

30. The composition of claim 22, wherein $R^4$ is —N=CRc—Ra or —CH$_2$—CO—Rb; Ra is substituted or unsubstituted phenyl with the substituents selected from the group consisting of lower alkyl, lower alkoxy, lower alkylthio, lower alkanoyl, lower alkoxycarbonyl, halogen, trifluoromethyl, hydroxy, nitro and cyano; and Rb is substituted or unsubstituted lower alkyl, lower alkoxy or phenyl with the substituents selected from the group consisting of one or two lower alkyl, lower alkoxy, lower alkylthio, lower alkanoyl, lower alkoxycarbonyl, halogen, trifluoromethyl, hydroxy, nitro and cyano.

31. The composition of claim 22, wherein $R^5$ is hydrogen.

32. The composition of claim 22, wherein $R^6$ and Rc are hydrogen.

33. The composition of claim 22 wherein said compound is 3-[p-(Chlorobenzylidene)amino]-1-[[p-(dimethylamino)-benzylidene]amino]-2-ethylimidazolium chloride.

34. The composition of claim 22 wherein said compound is 3-[p-(Dimethylamino)phenacyl]-1-[[p-(dimethylamino)benzylidene]amino]-2-ethylimidazolium chloride.

35. The composition of claim 22 wherein said compound is 1,3-Bis[[p-(dimethylamino)benzylidene]amino]-2-ethylimidazolium chloride.

36. The composition of claim 22 wherein said compound is 1-[[P-(Dimethylamino)benzylidene]amino]-2-ethyl-3-[(p-nitrobenzylidene)amino]imidazolium chloride.

37. The composition of claim 22 wherein said compound is 1,3-Bis[[p-(dimethylamino)benzylidene]amino]-2-propylimidazolium chloride.

38. An antibacterial, antimycotic, antiprotozoacidal or antihelminthic composition comprising a pharmcologically effective amount of an imidazolium compound, or a pharmaceutical acceptable acid addition salt thereof, and an inert carrier material wherein said compound has the formula

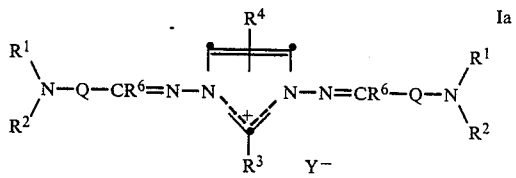

wherein Q is substituted or unsubstituted 1,4-phenylene or 1,4-naphthylene wherein the substituents are selected from the group consisting of one or two lower alkyl or lower alkoxy; $R^1$ and $R^2$ are each independently hydrogen or lower alkyl or taken together with the adjacent nitrogen atom are substituted or unsubstituted 4-morpholinyl, 1-piperazinyl, 4-(lower alkyl)-1-piperazinyl, 4-(lower alkoxy carbonyl)-1-piperazinyl, or 1-pyrrolidinyl with the substituents selected from the group consisting of one or two alkyl groups; $R^3$ is hydrogen, lower alkyl, lower hydroxyalkyl, lower alkoxyalkyl or lower haloalkyl; $R^5$ is hydrogen, lower alkyl, lower hydroxyalkyl, lower alkoxyalkyl, lower haloalkyl, a mono- or bicyclic carbocyclic aromatic group or is together with the atoms in the 4- and 5-positions of imidazole ring a benzene ring; $R^6$ is hydrogen or lower alkyl; the dotted line signifies an additional double bond; Y$^-$ is a pharmaceutically acceptable anion.

39. The composition of claim 38 wherein Q is 1,4-phenylene.

40. The composition of claim 39 wherein $R^1$ and $R^2$ are lower alkyl.

41. The composition of claim 40 wherein $R^3$ is lower alkyl; $R^5$ is hydrogen; and $R^6$ is hydrogen.

42. The composition of claim 38 wherein said compound is selected from the group consisting of 1,3-Bis[[p-(dimethylamino)benzylidene]amino]-imidazolium chloride, 1,3-bis[[p-(dimethylamino)benzylidene]amino]-2-methylimidazolium chloride, 1,3-Bis[[p-(dimethylamino)-benzylidene]amino]-2-ethylimidazolium chloride, and 1,3-Bis[[p-(dimethylamino)benzylidene]amino]-2-propylimidazolium chloride.

* * * * *